US012685555B2

(12) United States Patent
Fu et al.

(10) Patent No.: US 12,685,555 B2
(45) Date of Patent: Jul. 21, 2026

(54) SYSTEM AND METHOD FOR HARVESTING A TENDON

(71) Applicants:Smith & Nephew, Inc., Memphis, TN (US); Smith & Nephew Orthopaedics AG, Zug (CH); Smith & Nephew Asia Pacific Pte. Limited, Singapore (SG)

(72) Inventors: Rick Fu, Randolph, MA (US); Christopher David MacCready, Medfield, MA (US); Geoffrey Ian Karasic, Raynham, MA (US); Carrie Deborah Burgess, Jamaica Plain, MA (US); Belin Mirabile, Brookline, MA (US); Bernard Kilroy, Norwell, MA (US); Francheska Torres, Charlton, MA (US); Gregory Gorham, Billerica, MA (US); Miles Malone, Alameda, CA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 82 days.

(21) Appl. No.: 18/719,085

(22) PCT Filed: Dec. 16, 2022

(86) PCT No.: PCT/US2022/053098
§ 371 (c)(1),
(2) Date: Jun. 12, 2024

(87) PCT Pub. No.: WO2023/114447
PCT Pub. Date: Jun. 22, 2023

(65) Prior Publication Data
US 2025/0049465 A1     Feb. 13, 2025

Related U.S. Application Data

(60) Provisional application No. 63/290,362, filed on Dec. 16, 2021.

(51) Int. Cl.
*A61B 17/3205* (2006.01)

(52) U.S. Cl.
CPC ............................... *A61B 17/3205* (2013.01)

(58) Field of Classification Search
CPC .......... A61B 17/00008; A61B 17/0467; A61B 17/26; A61B 17/320016;
(Continued)

(56) References Cited

U.S. PATENT DOCUMENTS 6,117,152 A * 9/2000 Huitema ........ A61B 17/320092
601/2
6,179,852 B1 1/2001 Strickland et al.

FOREIGN PATENT DOCUMENTS

WO 2020/072766 4/2020

* cited by examiner

*Primary Examiner* — Elizabeth Houston
*Assistant Examiner* — Lindsey Bachman
(74) *Attorney, Agent, or Firm* — Kate Ryland Tetzlaff

(57) ABSTRACT

A system for harvesting a tendon graft is disclosed, the system including a retractor, a guide and at least one harvesting tool. The retractor holds open an anatomic space in a patient above the tendon. The guide assembles with the retractor to orient a guide shaft along the retractor and thereby the anatomic space. A first harvesting tool and the guide include a plurality of surfaces that cooperate with each other to transect the tendon and form at least one side of the tendon graft, the plurality of surfaces cooperating to limit a trajectory and a depth of cut into the tendon and also limiting both ends of the translational extent of the harvesting tool along the tendon. A second harvesting tool may extend along
(Continued)

the anatomic space formed by the retractor and form both a posterior cut along the tendon and transect a tendon graft end.

18 Claims, 19 Drawing Sheets

(58) Field of Classification Search
CPC ...... A61B 17/320036; A61B 17/32053; A61B
17/32056; A61B 17/3213; A61B 17/326;
A61B 2017/320028; A61B 2017/32004;
A61B 2017/320052; A61B 2017/320056;
A61B 2017/32113; A61B 2018/00428;
A61B 17/3209; A61B 17/322
See application file for complete search history.

3230c

POSTERIOR SIDE: CUT

SYSTEM AND METHOD FOR HARVESTING A TENDON

CROSS-REFERENCE TO RELATED APPLICATIONS

This application is the U.S. national phase entry under 35 U.S.C. 371 of International Application No. PCT/US2022/053098 titled "SYSTEM AND METHOD FOR HARVESTING A TENDON," filed Dec. 16, 2022, which claims benefit to U.S. Provisional Patent Application 63/290,362 titled "SYSTEM AND METHOD FOR HARVESTING A TENDON," filed Dec. 16, 2021, commonly owned and herein incorporated by reference in its entirety.

This application is related to International Patent Application PCT/US2021/036566, filed Jun. 9, 2021, and titled "SYSTEM AND METHOD FOR HARVESTING A TENDON"; commonly owned and herein incorporated by reference in its entirety.

FIELD

The present disclosure relates to a system and method for harvesting a tendon, and in particular for harvesting a Quadriceps Tendon (QT).

BACKGROUND

The quadriceps tendon is often used as a source of tissue graft for ligament surgery, such as anterior cruciate ligament (ACL) reconstruction. However, graft harvesting from the QT presents several challenges, as the QT is larger and stronger than other tendons, resulting in a tough fibrous bundle of tissue that tends to resist accurate consistent dissection. Furthermore, in order to reduce incisions around the target area, harvesting is preferably performed though a small incision near the knee. This may result in a second person retracting the skin away from the anterior QT surface while the surgeon wrestles with this tendon tissue. Existing devices may require multiple cuts to dissect this tough tissue. The fibrous tendon tissue may deviate related art devices from their intended cutting path, rendering an uneven and potentially useless graft strip cross section. Further difficulty occurs when terminating the graft at the proximal end of the strip, and at the furthest distance from the skin incision near the knee. Without making a larger or second skin incision, this proximal cut may be performed somewhat blind, and therefore time-consuming and risking inadvertent tissue damage. Therefore, there is a need for an improved system and associated method that can consistently remove a target sized strip of tendon tissue from the native tendon, overcoming the issues disclosed herein.

SUMMARY

Described herein is a system that includes a plurality of devices that may work together to harvest an autologous tissue graft from surrounding tissue, such as a tendon strip from the QT. Defining the entire QT as the native tissue, the system and methods described herein are configured to disconnect a portion or strip of this native tissue from itself. Before being harvested or disconnected, this resultant portion or strip is continuous with and non-discernable from the native QT tissue. Stated in another way, the portion or strip disconnected by the herein disclosed system is originally continuously coupled to the native tissue, along the entire length of the resultant strip, including at least three side surfaces of the resultant strip. The system that forms the graft strip dissects a continuous length through the native tissue along the entire length of the resulting strip or portion. The shape of the resultant portion or strip is defined by the system disclosed herein and can be altered with differing dimensions and methods of use of the disclosed systems and cutting tools.

Contrary to this, a vessel-harvesting tool for example, disconnects a target vessel from surrounding connective tissues along its length that may include smaller vessels and other connective and fatty tissues that are not remaining native vessel. It follows therefore, that this example harvested strip of vessel tissue (the target vessel) is disconnected from a plurality of tissues that are different from the target native vessel; the target native vessel is not a removed portion of itself along its entire length of the harvested vessel. The target native vessel is discernable from the connective tissue around it. It is coupled along its length to a plurality of tissues, and these tissues are different in composition to the target native vessel. In addition, continuing with a vessel-harvesting example, the vessel itself at least partially defines the shape and size of the harvesting tool and/or the resultant harvested tissue. As a further example, a polyp removal device disconnects a polyp from a substrate tissue, the polyp and substrate tissue not being the same tissue, and the polyp only coupled to the substrate at a first end of the polyp. In addition, the polyp is discernable from the substrate tissue and a device that disconnects a polyp does not define the boundary of polyp removed. The entire polyp is removed, the polyp defining the boundary.

Example systems for harvesting a tendon graft from a native tendon are disclosed herein, the systems including a guide and harvesting tool to interact. The guide may lie along an anterior surface of the native tendon and provide a static guide for the harvesting tool. The guide includes a handle end, a working end and an elongate shaft extending therebetween. The elongate shaft includes a first surface with indicative markings therealong. Indicative markings may be a plurality of laser markings indicating a length dimension for example. The harvesting tool may also include a handle end and a working end with an elongate shaft extending therebetween. The working end may include a blade for cutting into the native tendon and a channel for receiving the guide elongate shaft including the guide first surface and indicative markings therein. While the guide is held static, the harvesting tool may slide along the guide shaft. More specifically, the channel may slide along the guide elongate shaft including along the guide first surface and over the indicative markings. While sliding, the channel and guide shaft interact to limit both a depth and trajectory of the blade into and along the native tendon while also maintaining a wear-saving gap between the first surface and the channel to avoid contact with and potential damage to the indicative markings.

In some example systems, the channel has a bottom surface that faces the first surface when the channel is slides along the guide elongate shaft, the bottom surface and first surface spaced away from each other defining the wear-saving gap. In some example systems, the guide elongate shaft may include a tapered portion adjacent the handle end, the tapered portion configured to interact with the channel and gradually reduce a depth of the blade into the native tendon under the tapered portion as the harvesting tool slides along the tapered portion. In some example systems the guide shaft may include a projection with a channel, configured to slideably receive the harvesting tool shaft therein. The harvesting tool shaft may include a discrete projection sized larger than an opening size of the channel, configured to interact with the projection channel and limit a proximal translational extent of the blade along the guide shaft and thereby along the native tendon. The guide shaft projection may be disposed along the guide shaft at a location that limits the translational extent of the blade and prevents the blade from directly engaging the guide. The harvesting tool working end may be sized larger than the opening size of the projection channel, to limit a distal translational extent of the blade along the guide shaft. The indicative markings may include a distal-most reference marking, and wherein the harvesting tool working end and guide shaft projection are configured to interact and limit a distal translational extent of the blade to prevent the blade from cutting the native tendon distal to the distal-most reference marking. The guide working end may be configured to bluntly dissect tissue away from an anterior surface of the native tendon.

Another example system disclosed herein includes a system for harvesting a portion of tendon graft from a native tendon, the system including a guide and a harvesting tool. The guide may generally be placed along the native tendon and may include a handle end, a working end and an elongate shaft extending therebetween. The elongate shaft may include indicative markings along a first surface of the elongate shaft. The indicative markings are visible to the user while the guide is placed along the native tendon and may indicate a length or distance along the shaft for judging a length of tendon graft or available native tendon for example. The harvesting tool may include a handle end and a housing at an opposing working end. The housing may selectively couple to a blade. The housing may include at least one surface configured to slidingly engage the guide elongate shaft and guide a cutting trajectory and depth of the blade into the native tendon. The housing may slidingly engage the guide elongate shaft while sliding over but spaced away from the indicative markings to form a wear-saving gap over the indicative markings.

In some example embodiments, the harvesting tool housing may include a channel with a bottom surface that faces the indicative markings while the housing slides along the guide elongate shaft, the bottom surface and indicative markings spaced away from each other defining the wear-saving gap. In some example embodiments, the guide elongate shaft may include a tapered portion adjacent the handle end thereof, that interacts with the harvesting tool to gradually reduce a depth of the blade into the native tendon as the harvesting tool blade slides along the tapered portion. In some example embodiments, the guide shaft includes a goal post configured to slideably receive the harvesting tool shaft therein, and wherein the harvesting tool shaft includes a discrete projection configured to interact with the goal post and limit a proximal translational extent of the blade along the guide shaft and thereby along the native tendon. The harvesting tool housing may also engage the goal post and limit a distal translational extent of the blade along the guide shaft. The system may also include a proximal cutter having a leading-edge surface that is linear, configured to forming a posterior cut along the native tendon and another edge surface configured to transect an end of the tendon graft after the poster cut is formed.

Disclosed herein is a surgical device for harvesting a tendon graft from a native tendon, the device including a handle for manipulating the surgical device, a shaft extending from the handle and a working end extending from the shaft. The working end may selectively couple to and house a blade. The blade defines a thin planar element, and wherein the blade is axially slideable relative to the working end between an open configuration and a transected configuration. The blade includes an aperture though a thickness of the thin planar element, having an opening sized for receiving a strip of tendon graft therethrough. An edge portion of the aperture defines a cutting edge-surface. The blade also includes a leading edge-surface defining a cutting surface and separate from the aperture. The blade is in the open configuration advancing the surgical device is configured to form a posterior side of the tendon graft with the leading cutting edge-surface and wherein when the blade is moved to the transected configuration the aperture edge portion is configured to cooperate with an edge of the working end to transect the tendon graft.

In some embodiments, the aperture is recessed within the working end when in the transected configuration. In some embodiments, the leading cutting edge-surface may define the furthest most edge of the surgical device when the blade is in the open configuration. In some embodiments, the aperture includes another edge portion continuous with the aperture edge portion and that defines a blunt surface that limits cutting into an anterior surface of the native tendon while the surgical device advances along the native tendon and forms the posterior side of the tendon graft. In some embodiments, the leading edge-surface may define a varying profile such that an edge-surface portion closer to the longitudinal axis is sharp and become gradually blunter as it extends away from the longitudinal axis.

BRIEF DESCRIPTION OF THE DRAWINGS

The disclosure will be more fully understood by reference to the detailed description, in conjunction with the following figures, wherein.

DETAILED DESCRIPTION

Figure 1:
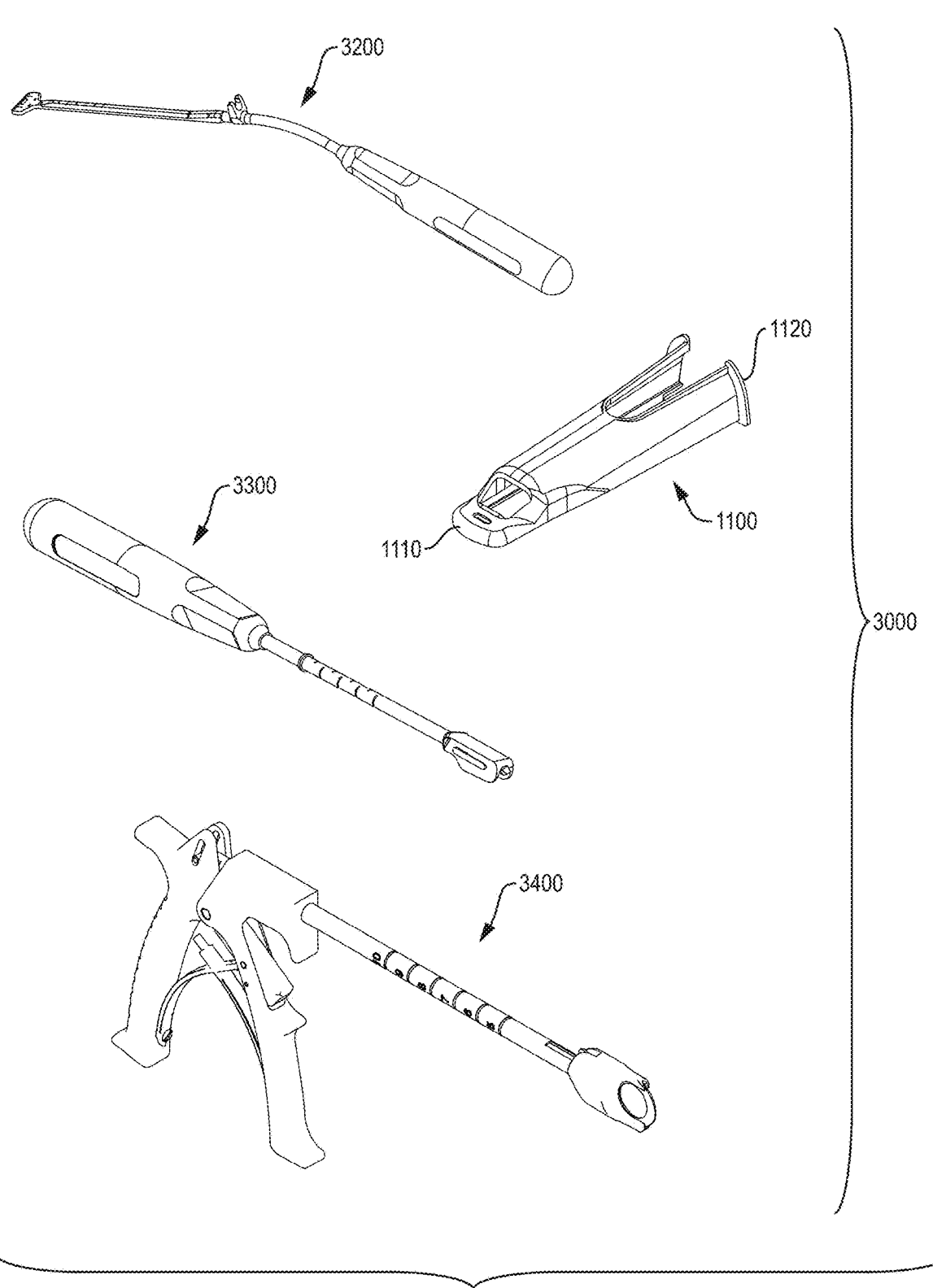
FIG. 1 illustrates an overview of an example tendon harvesting system, in accordance with this disclosure.
Figure 2A:
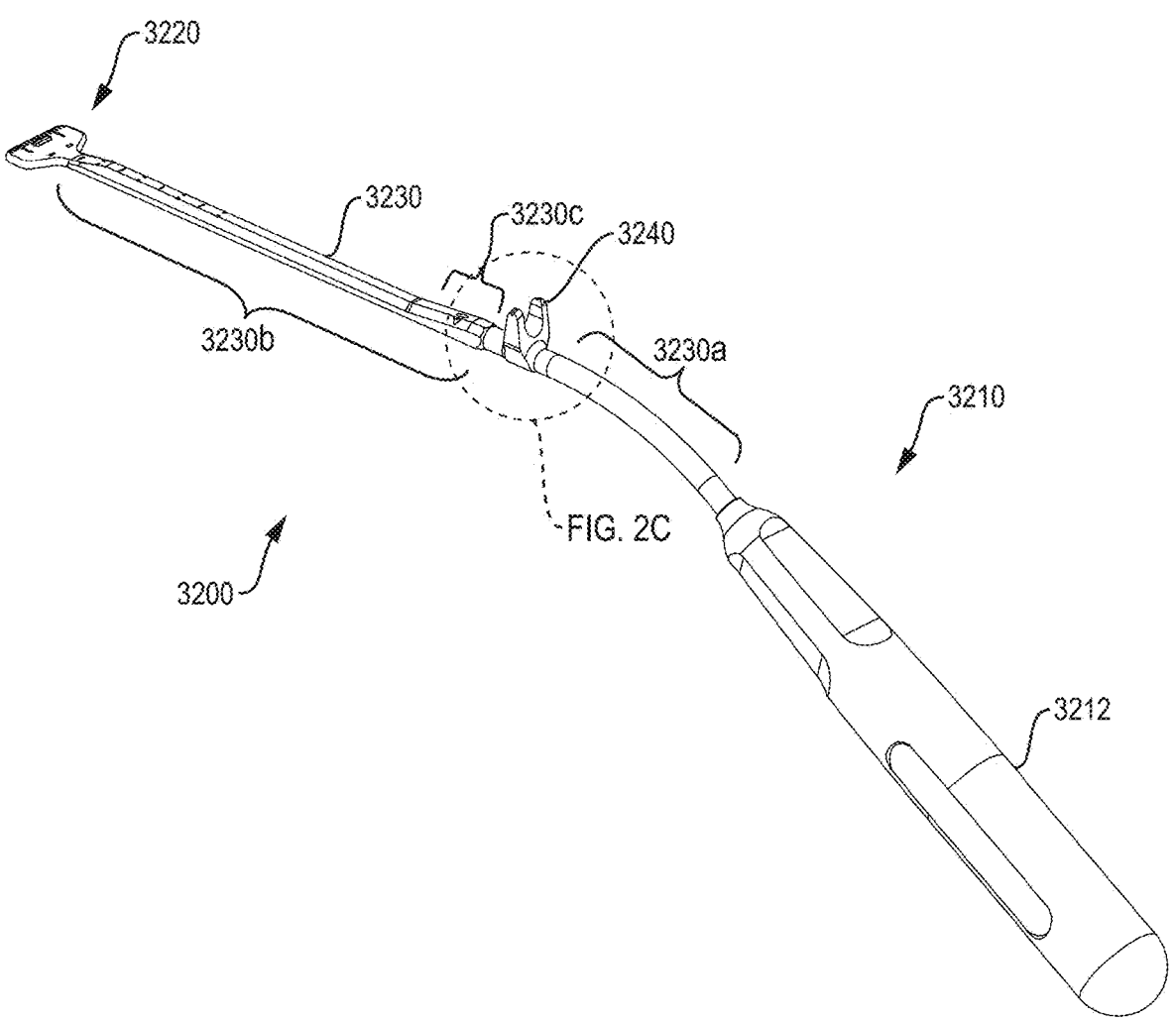
FIG. 2A illustrates an isometric view of a blunt dissector/guide of this disclosure.
Figures 2B, 2C, 2D:
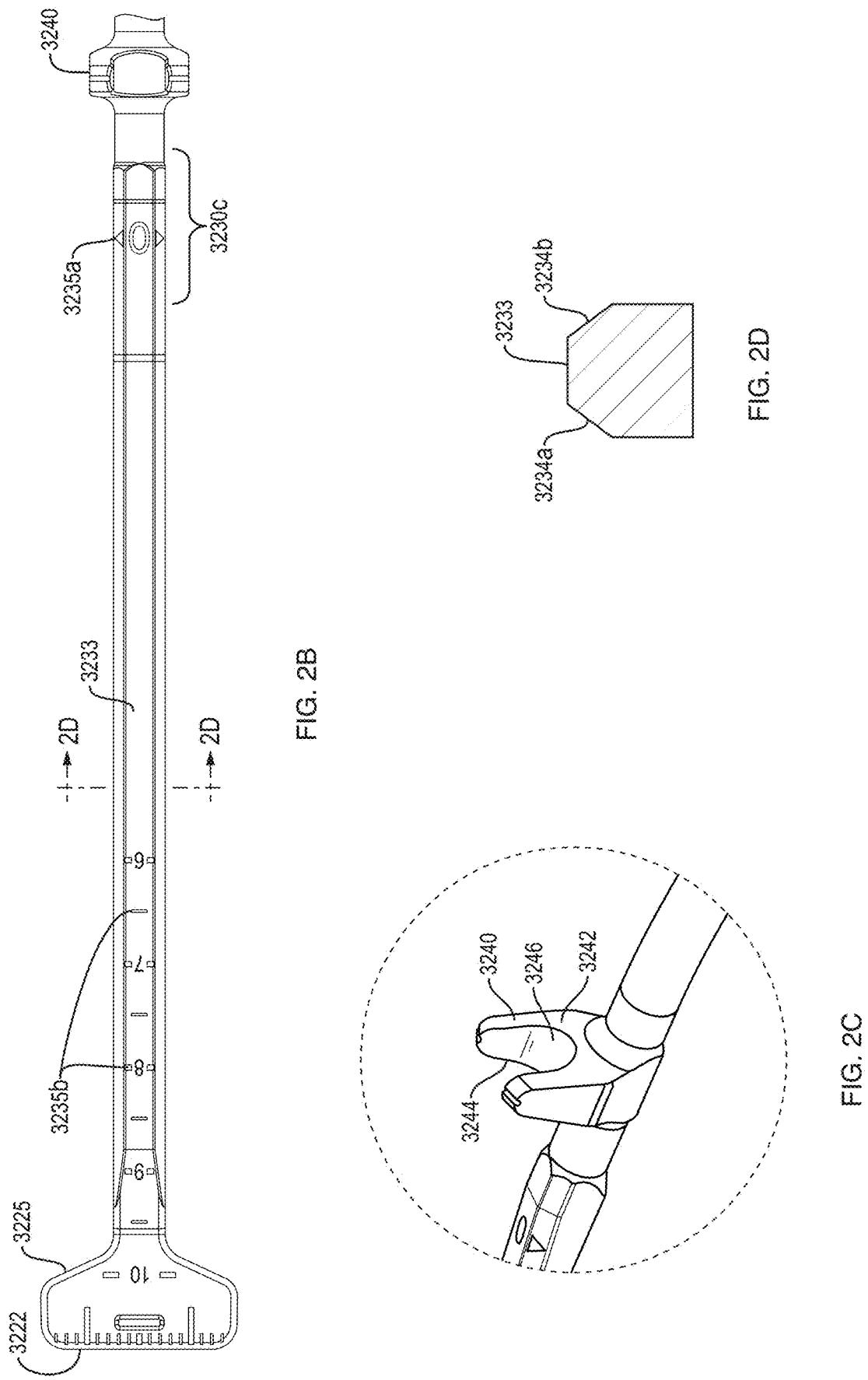
FIG. 2B illustrates a top view of the guide of this disclosure.
FIG. 2C illustrates a close up of a goal post of the guide of this disclosure.
FIG. 2D illustrates a cross section of the guide shaft of this disclosure.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/ or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open-ended, include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Referring now to FIG. 1, an overview of an example system 3000 is illustrated, including retractor 1100 and a plurality of instruments including but not limited to a blunt dissector/guide 3200, harvesting tool 3300 and proximal cutter 3400. Blunt dissector 3200 may sometimes be used as a tissue dissector, and sometimes as a guide, and hereinafter will be called "guide". All or some parts of the disclosed system may be used, in combination with other instrumentation to harvest a tendon strip or graft from a native tendon 50. The system 3000 is configured to remove a strip of tendon tissue from the native tendon, consistently and reliably, according to a predetermined strip length, width and depth. The system 3000 may be configured to lie along a patient's leg, between the patient knee and a proximally disposed quadriceps muscle of the same leg. As such, throughout this disclosure, the term "distal" relative to portions of the system define portions closer to the knee, and the term "proximal" define portions of the system that are closer to the patient thigh or quadriceps muscle. Stated in another way, the terms proximal and distal relate to the patient throughout this specification, rather than the tool user. Portions of system 3000 may operate in a similar manner to the systems disclosed in International Patent Application PCT/US2021/036566, filed Jun. 9, 2021, and titled "SYSTEM AND METHOD FOR HARVESTING A TENDON"; commonly owned and herein incorporated by reference in its entirety.

The system 3000 includes a retractor 1100 that is self-supporting and may be configured for insertion into a small incision near the knee. Retractor 1100 is preferably placed subcutaneously, and both along and on the anterior surface of the Quadriceps Tendon, hereinafter "QT". Retractor 1100 forms a working cavity for access to and visibility of the QT. Retractor 1100 is configured to provide access for the plurality of instruments of the system to the tendon via the working cavity. Retractor 1100 is configured to hold the working cavity open or tent the skin away from the tendon anterior surface without requiring external forces and is thereby self-supporting. Example external forces (that are not required) may include a positioning arm or stand, a robot arm, or a second person holding a paddle retractor. Retractor 1100 is configured to operatively interact with the plurality of instruments, such as guide 3200, harvesting tool 3300 and proximal cutter 3400, while forming the strip of tendon tissue. Operatively interacting may include receive at least one of the plurality of instruments therein and/or operatively engage with and/or guide the plurality of instruments.

The guide 3200 may perform a plurality of functions, both independent of other portions of the system 3000, and also while assembled thereto. For example, the guide 3200 may dissect or separate tissue before the retractor 1100 is inserted. Guide 3200 may also operatively couple to the retractor 1100 to provide a handle for inserting and placing the retractor 1100. Guide 3200 may also provide a trajectory guide to limit the trajectory of the harvesting tool 3300. In some system embodiments, a separate tool other than or in addition to guide 3200 may dissect the tissue first. The harvesting tool 3300 may be configured to form two lateral sides of the tendon strip simultaneously, from medial and lateral sides of the native tendon. Harvesting tool 3300 may use portions of the retractor 1100 and guide 3200 as a guide to control the cut trajectory and cut depth posteriorly into the native tendon. The proximal cutter 3400 may slide along the retractor's working cavity and form a posterior side surface of the tendon strip. Upon reaching a proximal end of the native tendon, the proximal cutter 3400 may also transect the proximal end of the tendon strip from the native tendon.

Turning now to the details of the individual components of system 3000, details of retractor 1100 are disclosed in International Patent Application PCT/US2021/036566, filed Jun. 9, 2021, and titled "SYSTEM AND METHOD FOR HARVESTING A TENDON"; commonly owned and herein incorporated by reference in its entirety. Retractor 1100 may be a unibody or single molded element, formed of a flexible material. Retractor 1100 is configured to be collapsed or reduced in profile and then inserted through an incision and under the skin. Once inserted, retractor 1100 is generally self-supporting and configured to hold open the anatomic space it is inserted into for performing minimally invasive surgical procedures. The retractor 1100 defines an elongate body, with proximal and distal ends, and may have a general arch shape or "C" shaped cross-section, defining a passage and longitudinal working cavity therealong. Retractor 1100 preferably includes a rounded, tapered or streamlined shape along its length to facilitate insertion along the dissected space anterior of the tendon, with minimized tissue trauma. Retractor 1100 proximal end 1110 may be enclosed, with a lower profile than distal end 1120. Retractor 1100 may be formed of a plastic and may be translucent to facilitate better tissue visualization. In addition to being formed of a flexible material, retractor 1100 also includes a plurality of reliefs to improve elastic deformation of the retractor 1100, for easier insertion through the incision and under the skin. However, the retractor 1100 is sufficiently rigid to return towards its non-deformed shape once under the skin and push the skin up to form a tent or working cavity. This provides the surgeon with a working cavity on the target tendon, the tendon readily visualized through the incision and open distal end 1120 of retractor 1100.

Details of the blunt dissector/guide 3200 are illustrated in at least FIGS. 2A-2D. Guide 3200 is similar to guides disclosed in International Patent Application PCT/US2021/036566, filed Jun. 9, 2021, and titled "SYSTEM AND METHOD FOR HARVESTING A TENDON"; commonly owned and herein incorporated by reference in its entirety, with some improvements, as disclosed herein. Guide 3200 generally includes a handle end 3210, working end 3220 and a shaft 3230 extending therebetween. Working end 3220 may include a leading edge 3222 that may be linear across its extent and is generally blunt and configured to separate tissue layers. Guide 3200 may be used to bluntly dissect tissue and may be inserted through incision near the superior pole of patella and advanced under the skin, to bluntly separate the skin layers from the anterior QT surface. As such, leading dissecting edge 3222 is preferably not so sharp to cut or pierce the tendon or skin layers. It may however break through connective tissue connecting the QT anterior surface from the skin layers. Guide 3200 may be configured to clear away the fat pad under the skin. Guide 3200 may perform this separation before inserting the retractor 1100.

Handle end 3210 may be angularly offset from the working end 3220 and proximal length shaft portion 3230*b*. Shaft 3230 may include a bend, forming the angular offset. Shaft 3230 defines a distal portion 3230*a*, extending directly from handle 3212. Shaft distal portion 3230*a* may define a first cross section that is circular. Angular offset may be formed by a curve or bend along the distal portion 3230*a*. Angular offset may be between 140-160 (°) degrees and is configured to align the shaft proximal portion 3230*b* along the tendon surface while angling the handle 3212 around a bent knee and out of the way. Shaft proximal portion 3230*b* may be non-circular in cross section. Proximal portion 3230*b* may define a straight linear length, configured to lie on or lie parallel to the relatively flat QT anterior surface. In some embodiments, working end 3220 may include indicators or markings along the leading edge 3222, oriented transverse the longitudinal axis of the shaft 3230 for estimating a width of native tendon 50 tissue available for harvesting. Working end 3220 may be wider than shaft 3230 and may be termed a spatula end. A tapered edge 3225 may extend between the shaft proximal portion 3230*b* and leading edge 3222. Tapered edge 3225 may extend bilaterally from both sides of the shaft 3230 and, in some embodiments, may include a scalloped or cutting edge (not shown) that may dissect connective tissue while retracting the blunt dissector/guide 3200 (moving it towards the knee/distally).

Figure 6A:
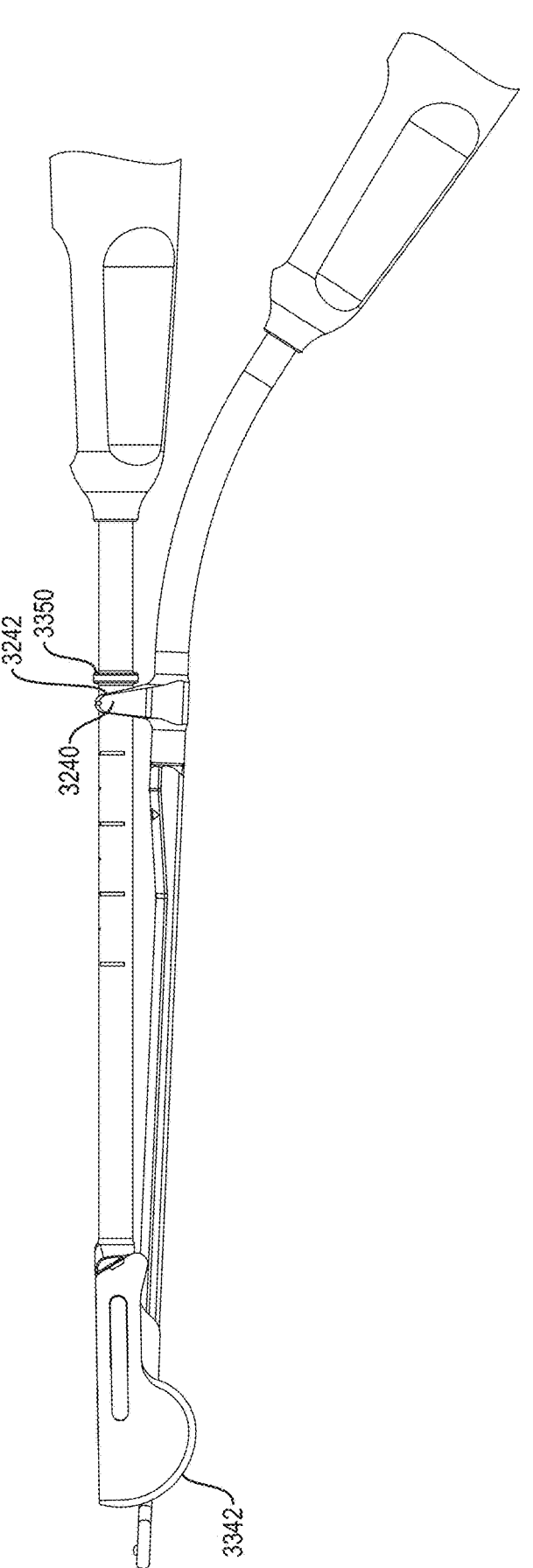
FIG. 6A illustrates a side view of the guide with the harvesting tool at a proximal limit of its translation, with the harvest tool annular ring and goal post engaged, in accordance with this disclosure.
Figure 6B:
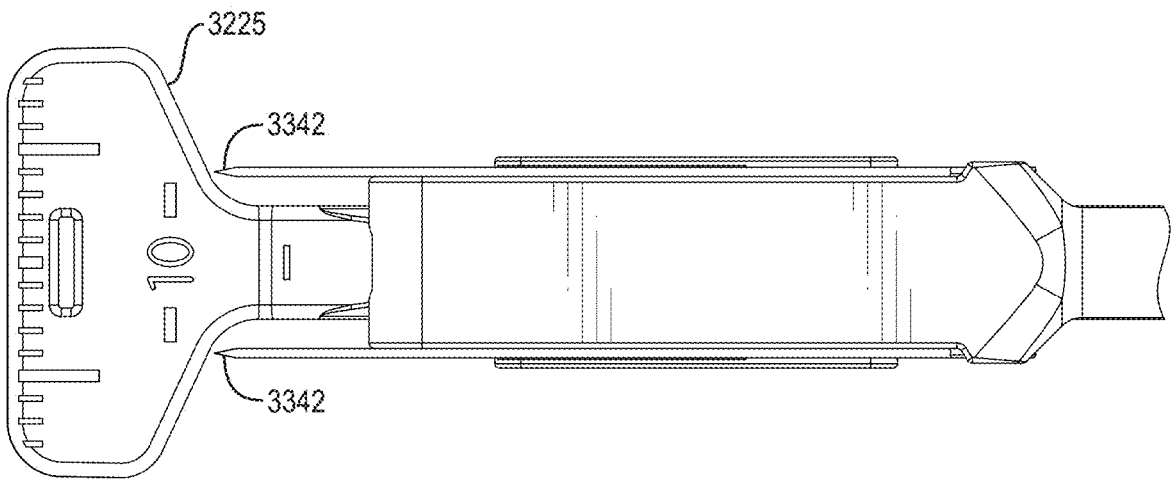
FIG. 6B illustrates a top view of the guide with the harvesting tool at a proximal limit of its translation and with the harvesting tool blades axially spaced therefrom, to avoid any damage to the blades, in accordance with this disclosure.
Figure 6C:
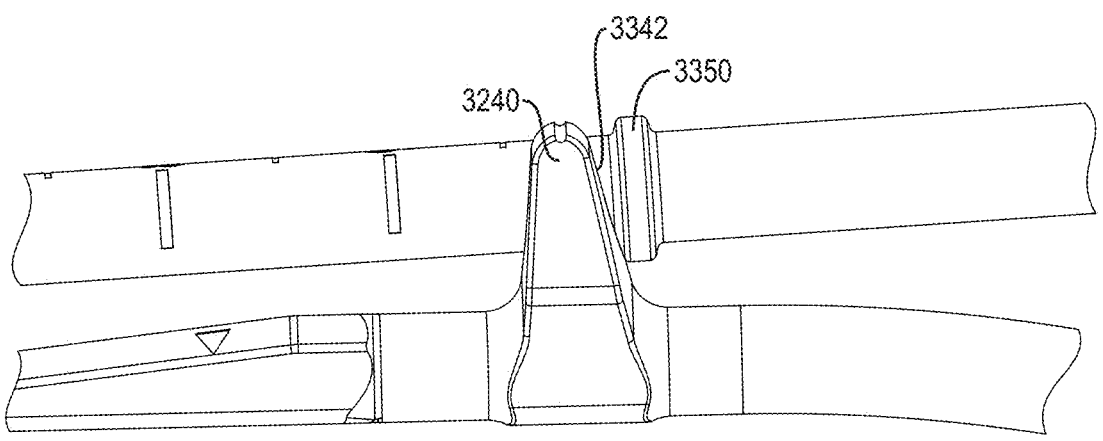
FIG. 6C illustrates a side view of the guide goal post with the harvesting tool annular ring in engagement in accordance with this disclosure.
Figure 6D:
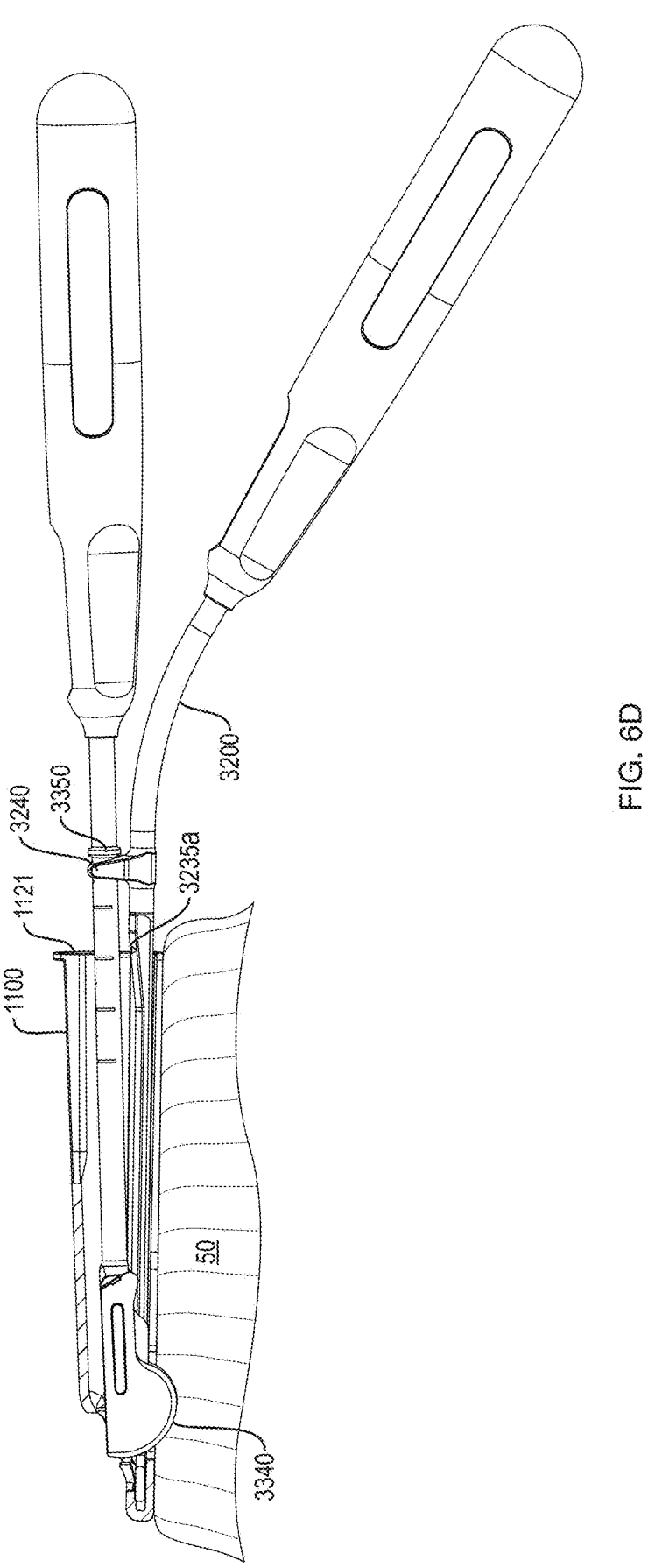
FIG. 6D illustrates a side view of the system with a portion of the retractor removed, with the guide disposed therein and with the goal post engaged with the harvesting tool annular ring, in accordance with this disclosure.
Figure 7:
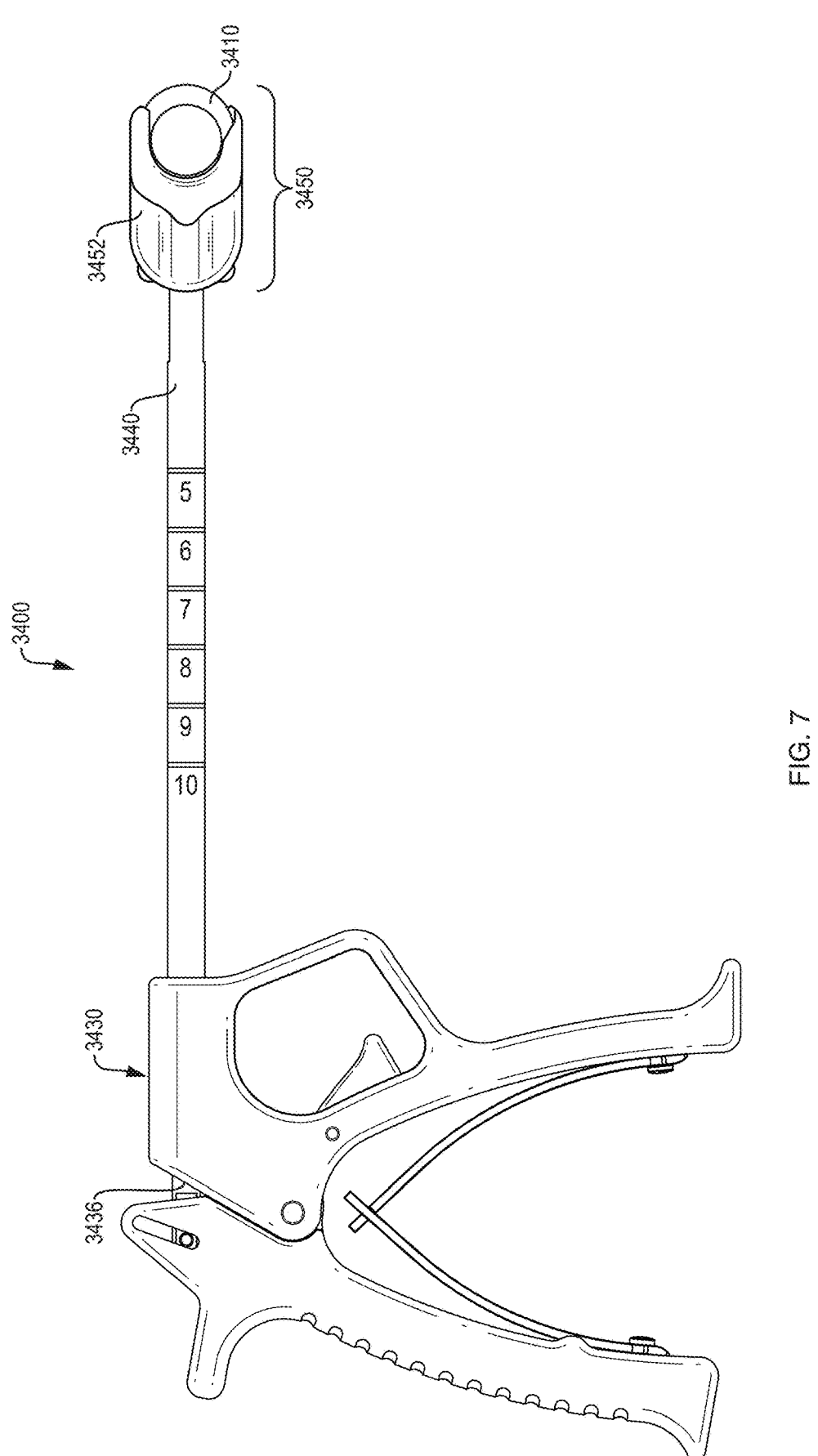
FIG. 7 illustrates a view of a proximal cutter, in accordance with the disclosure.

Shaft proximal portion 3230*b* may include markings 3235 thereon, used to estimate a length of native tendon 50 available to be harvested. Markings 3235 may also be used to estimate a length of resulting tendon strip being formed, as will be described in more detail hereinafter. Markings 3235 may include a reference mark 3235*a* that may be zero. Reference mark 3235*a* may be a distal-most mark of the markings 3235. When working end 3220 is engaged with retractor 1100, reference mark 3235*a* may align with a distal edge of retractor distal opening 1120 (FIG. 6D). Proximal markings 3235*b* may include numerical markings corresponding with a distance from reference mark 3235*a*. Markings 3235*b* may help to estimate a length from reference marking 3235*a*, and thereby aid in estimating a length of native available for harvest. Proximal markings 3235*b* may indicate a distance in inches or centimeters from reference marking 3235*a*. In use, the retractor 1100 may be placed at an incision opening near the patella, and therefore the markings 3235*b* may indicate an estimated length from the incision opening along the native tendon 50. Markings 3235 may be on a top surface 3233 of proximal shaft portion 3230*b*, for direct visualization through the plurality of openings through the retractor 1100, and also through the opaque retractor body and/or through a camera inserted along the retractor 1100 during use. Markings 3235 may be laser marking.

Guide 3200 cooperates with harvesting tool 3300 to define the trajectory of the harvesting tool 3300 along and into the native tendon 50. Shaft portion 3230*b* is shaped to cooperate with harvesting tool 3300 to define the trajectory, in a similar manner to the guide and harvester disclosed in Patent Application PCT/US2021/036566, filed Jun. 9, 2021, and titled "SYSTEM AND METHOD FOR HARVESTING A TENDON"; commonly owned and herein incorporated by reference in its entirety, with some improvements as disclosed herein. In a similar manner, harvesting tool 3300 (disclosed in more detail hereinafter) may engage and slide along surfaces of the guide 3200 to define the cut trajectory and depth of cut into the tendon. However, in some example embodiment systems, guide 3200 may be a reusable device and sterilized between uses. Repeated sliding of a harvesting tool 3300 along surfaces of the guide 3200 may lead to surface wear with repeated uses. It is therefore preferable that guide surfaces that cooperate and engage with the harvesting tool 3300 do not include surfaces with the markings 3235 thereon, as these markings 3235 may be gradually removed over time as the surfaces wear. Therefore, guide 3200 preferably includes at least one surface, easily visualized during use that includes markings 3235 for enabling the harvesting procedure, such as estimating a graft or tendon length; the surface spaced away from the harvesting tool 3300 during use to preserve the surface. More specifically, guide 3200 may include a surface that includes markings therealong, the surface bordered by another surface that slidingly engages a mating harvesting tool, this other surface defining a trajectory and cutting depth of the harvesting tool while leaving the surface including the markings free from engagement with the harvesting tool. Best seen in FIG. 2D, shaft proximal portion 3230*b* may define a cross section with multiple facets, including a top surface 3233 that may include markings 3235, and bilateral angled surfaces 3234*a*, 3234*b* bordering the top surface 3233, one each side. Shaft cross section may be configured to preferably slidingly engage with a harvesting tool 3300 on at least surfaces 3234*a*, 3234*b* while forming a marking-saving or wear-saving gap (X) (FIG. 4B) to avoid any sliding engagement and therefore wear on top surface 3233.

While slidingly engaged, the harvesting tool 3300 may form a medial and lateral cut along the native tendon 50, at a cutting depth defined at least partially by surfaces 3234*a*, 3234*b* and the shaft proximal portion thickness. This shaft thickness is generally consistent along the length of the shaft proximal portion 3230*b*, with a tapered increase towards a distal end, best seen in FIGS. 5D and 6C. This taper elevates surfaces 3234*a* and 3234*b* further from the tendon anterior surface and forms a shallower cutting depth into the native tendon 50 at the distal end thereof. This may reduce any damage to tissues below the native tendon 50 at the distal end. The native tendon 50 may be shallower at its ends. Reference marking 3235*a* may lie along this tapered portion 3230*c* of shaft. In some other embodiments, one skilled in the art may not necessarily increase the shaft thickness but may angularly offset the shaft 3230 in a direction away from the tendon anterior surface.

Guide 3200 may also include a projection, that may be in the form of a goal post 3240 projecting from shaft 3230. Goal post 3240 may project from a top side of shaft 3230, on the same side as top surface 3233. Goal post 3240 may define a channel 3246 for receiving a shaft 3330 of a harvesting tool 3300 therein. Goal post channel 3246 may be deep enough to retain the harvesting tool shaft 3330 within the channel 3246 for a range of angles between the harvesting tool 3300 and guide 3200, such as angles shown in FIGS. 5E and 6D. The harvesting tool shaft 3330 may slide therethrough while cutting the native tendon 50, disclosed in further detail hereinafter. Goal post 3240 includes a first surface 3242 configured to limit a first end of a translation extent of the harvesting tool 3300. First surface 3242 may be a distal surface of goal post 3240. Goal post 3240 may also include a second surface 3244 that may be on the opposing side of the goal post 3240 to the first surface 3242 and may define a second end of a translation extent of the harvest tool 3300. The second surface 3244 may cooperate with the harvesting tool 3300 and stop the harvesting tool 3300 from further distal translation at a location that stops a blade edge of the harvesting tool 3300, so that the blade leading-most edge aligns with the reference marker 3235*a*. The first and second ends or limits of the translation extent may define the maximum length of graft tendon to be harvested. Goal post 3240 may be positioned so as to be external to and distal to the retractor 1100 while the guide 3200 is engaged with retractor proximal end 1110. Stated in another way, guide 3200 is configured to operatively couple to the retractor 1100 and position the goal post 3240 outside of the retractor 1100.

Figure 3A:
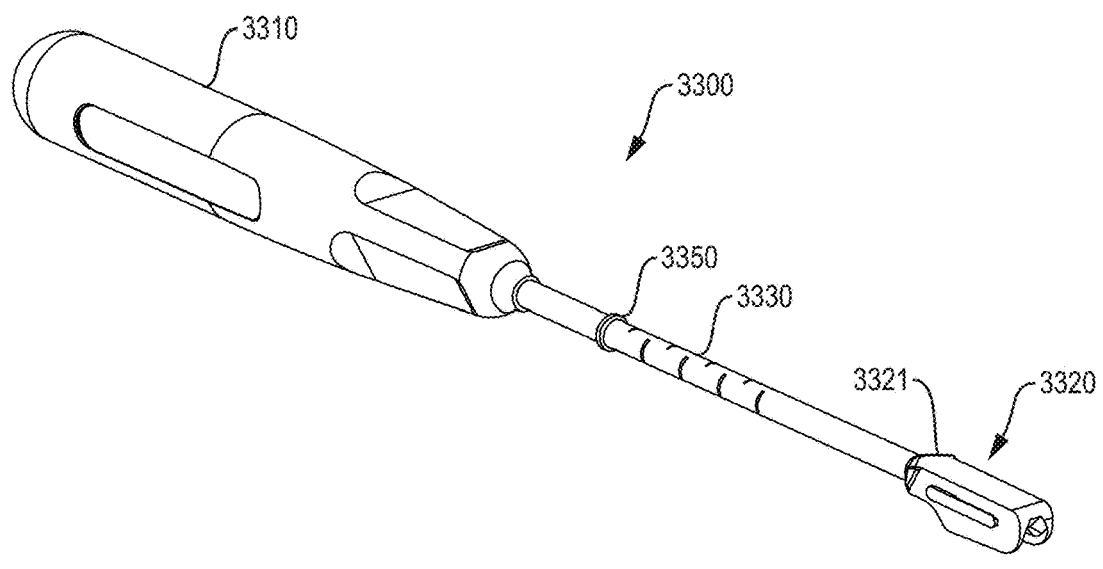
FIG. 3A illustrates an isometric view of a harvesting tool with blades attached thereto, in accordance with this disclosure.
Figure 3B:
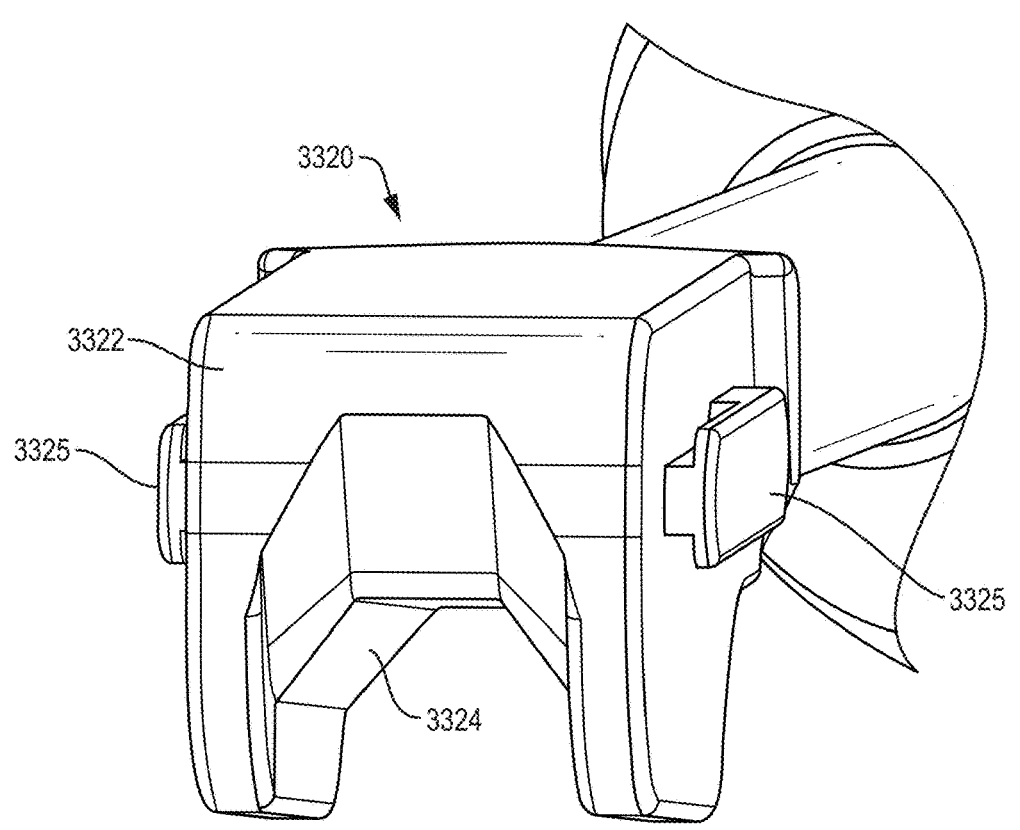
FIG. 3B illustrates a view of the working end of the harvesting tool without the blades attached thereto, in accordance with this disclosure.
Figure 3C:
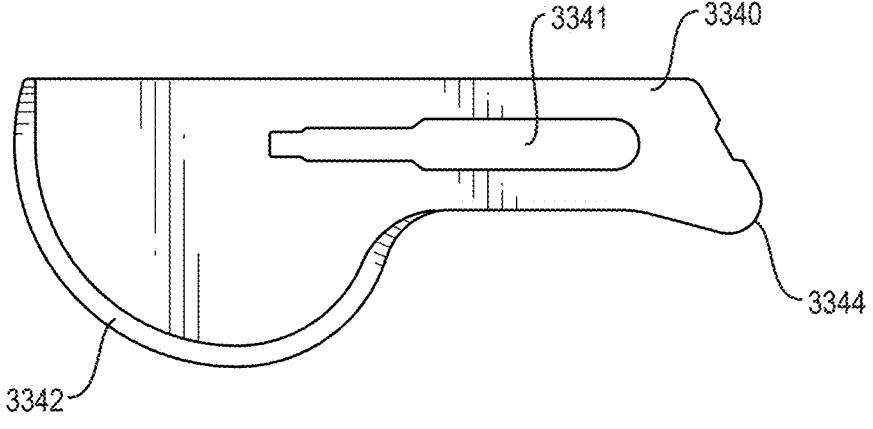
FIG. 3C illustrates a view of one of the blades for the harvesting tool, in accordance with this disclosure.

FIGS. 3A-3C illustrates various views of a harvesting tool 3300, that may cooperate with guide 3200 and may couple to and operate at least one blade 3340. Harvesting tool 3300 may couple to two of these blades 3340 in a parallel arrangement, to form two sides of a tendon strip simultaneously. Relative to the patient, harvesting tool 3300 may forms two elongate cuts along the native tendon 50, including a lateral and medial cut. Harvesting tool 3300 includes a handle 3310 and working end 3320, with an elongate shaft 3330 therebetween. Shaft 3330 and handle 3310 may both lie along the same linear longitudinal axis. In other words, handle 3310 and shaft 3330 may not include any bend or angular offset, such as the bend along the guide 3200. Working end 3320 may include a housing 3322 fixedly coupled to shaft 3330, housing 3322 including engagement means 3325, each engagement means 3325 configured to selectively attach to at least one blade 3340. Engagement means 3325 may be disposed, one each side of the housing 3322. Engagement means 3325 may include elongate tabs, and may be disposed, one each, on lateral external surfaces of housing 3322. Engagement means 3325 may be oriented at an angle that defines a location of a leading cutting edge 3342 of a blade 3340 and thereby at least partially defines a depth of cut into the native tendon 50. (As explained earlier, a thickness of the guide shaft, that may be tapered along portions, also may partially define the depth of cut). Blade 3340 is shown in FIG. 3C. One blade 3340 may couple to a first lateral side of the housing 3322 and a second blade 3340, that may be a copy of the first blade 3340 may couple to an opposing lateral side of the housing 3322. Each blade 3340 may have a slot 3341 for interfacing with the engagement means 3325. Blade 3340 may have a curved cutting edge 3342 that is a single and continuous curve. Cutting edge 3342 may form a segment of a circle and therefore cutting edge may have a constant radius. Cutting edge 3342 may extend along a curved path sufficient that the cutting edge 3342 may face both proximally and distally. This may provide cutting while both retracting and advancing the blades 3340. Also, a continuous curve along the cutting edge 3342, with no discontinuities therealong may slide more evenly and predictably along and through the tissue. A cutting edge with a pointed end or apex, similar to the standard scalpel blade for example disclosed in Patent Application PCT/US2021/036566, filed Jun. 9, 2021, and titled "SYSTEM AND METHOD FOR HARVESTING A TENDON" may tend to dig into and lift the native tendon 50 tissue, possibly resulting in an uneven cutting depth into the native tendon 50.

In addition, the inventors have found that it is preferable that blades 3340 be single use so as to provide consistent sharpness and thereby consistent cutting for each procedure. Sterilization methods for reusable surgical tools tend to dull sharp edges. An opposing 3344 end of blades 3340 may preferably extend further than housing 3322 when assembled thereto. Opposing end 3344 may define a handle end of the blade 3340 and be blunt and safe to hold by hand without cutting. This may provide an end 3344 readily graspable for assembling and removing blade 3340 from housing 3322.

Harvesting tool 3300 may be provided as part of a kit with a plurality of configurations that correspond to selectable widths and depths of cut through and along the native tendon 50. The different configurations may have differing housing widths or heights and/or different curvatures or radii of blade cutting edge 3342. The two blades 3340 may preferably be assembled parallel to each other, and form two equivalent cut depths into and along the native tendon 50 simultaneously. Example lateral distances between blades 3340, defined by a width of housing 3322 may be between 5-15 mm, and may more preferably be between 8-12 mm. For example, a kit may include three harvesting tools, one with a housing width of 8 mm, one with a housing width of 10 mm and one 12 mm, each for forming a tendon graft width of about the width corresponding to the housing width.

Turning now to FIG. 3B, housing 3322 defines a lower surface that may include an elongate channel 3324, the channel having a cross section that receives guide proximal shaft 3230*b* therein. Channel 3324 may cover shaft 3230*b* and slide along shaft 3230 while forming the graft lateral sides (via blades 3340). Channel 3324 may define a cross section shape that may form a sliding fit with at least two external surfaces of guide proximal shaft 3230*b*. Channel 3324 may engage and slide along mating surfaces 3234*a*, 3234*b* of guide. Channel 3324 may cover top surface 3233 of guide shaft 3230 but remain spaced way from this top surface 3233 to avoid wear of surface 3233 and thereby avoiding removal or fading of markings 3235 thereon.

The channel 3324 and guide proximal shaft 3230*b* are configured to guide the trajectory and depth of cut of the harvesting tool 3300 and thereby the blades 3340 along the retractor 1100 and into the native tendon 50. The lower surface 3231 of guide 3200 may engage the tendon anterior surface. In other embodiments, only the bottom surface of retractor 1100 may engage the QT anterior surface. Depth D of cut may therefore be defined and controlled by the configuration of blades 3340, the configuration of housing channel 3324 and the configuration of the proximal and tapered guide shaft 3230*b*, 3230*c*. Stated another way, the depth D of cut may be defined by the blade configuration and interaction of the housing channel 3324 with the guide shaft 3230.

Figure 4A:
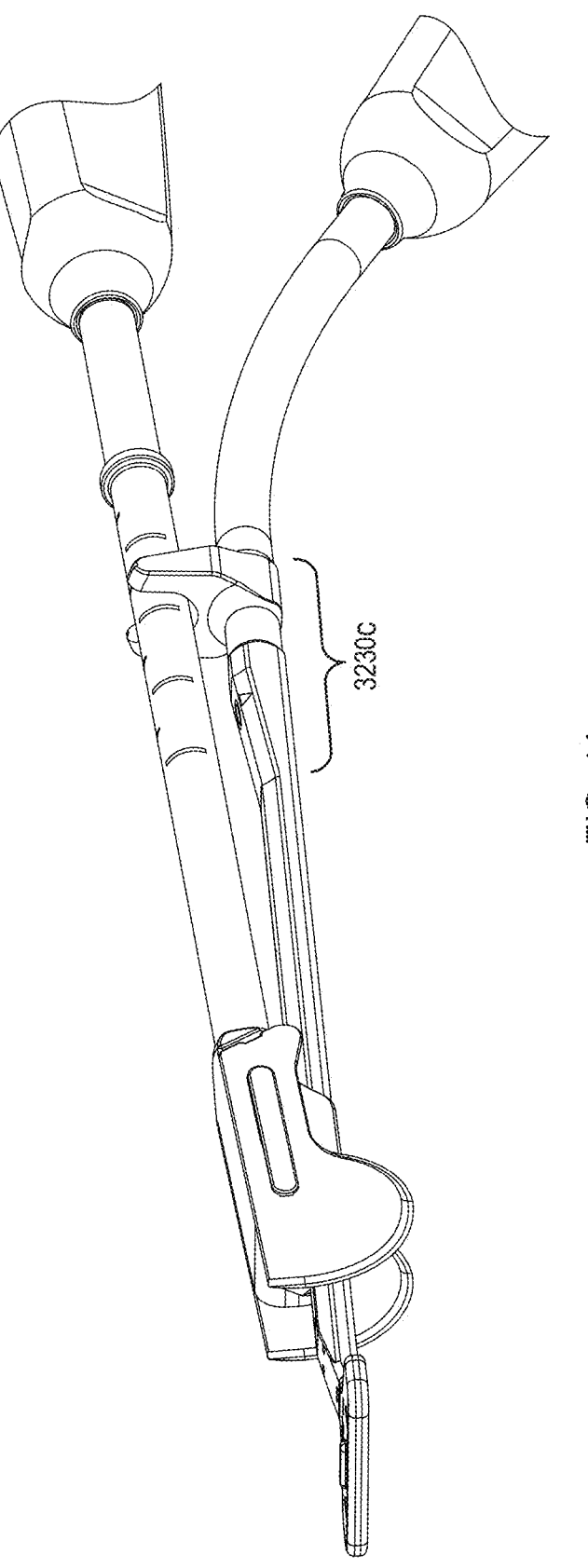
FIG. 4A illustrates a perspective view of the harvesting tool sliding along the guide, in accordance with this disclosure.

Harvesting tool 3300 may also include a stopping projection that may be in the form of an annular ring 3350 around shaft 3330. Ring 3350 may be fixed to shaft 3300 and may be disposed towards a distal end of shaft 3300, closer to the handle 3310 than housing 3320. Ring 3350 may form a complete ring (360 degrees) around shaft 3330. In other embodiments, ring 3350 may be interrupted around its circumference, or oblong in cross section. Ring 3350 is configured to interact with goal post 3240 and limit a proximal extent of harvesting tool 3300 relative to the guide 3200. In use, shaft 3330 is placed within goal post channel 3246. Harvesting tool 3300 may be advanced and retracted along the guide tapered shaft portion 3230C and proximal guide portion 3230*b*, while the harvesting tool shaft 3330 is disposed at least partially within the goal post channel 3246. Harvesting tool 3300 may be advanced and retracted along native tendon 50, with the harvesting tool housing channel 3324 engaging surfaces 3234*a*, 3234*b* of the guide 3200 while the harvesting tool shaft 3330 is disposed within goal post channel 3246, as best viewed in FIGS. 4A and 5C.

Annular ring 3350 defines a radius or outermost dimension that is larger than an opening side of channel 3246 so as to prevent entry of the ring 3350 into the channel 3246. Annular ring 3350 therefore defines a stopping projection that limits harvesting tool advancement. Annular ring 3350 defines a radius or outermost dimension that interacts with goal post 3240 to limit how far the harvesting tool 3300 may advance. This proximally limited position is illustrated in FIGS. 6A-6C, wherein annular ring 3350 abuts a surface 3242 of goal post 3240 and therefore blade edge 3242 may no longer advance proximally. The cooperation between the goal post 3240 and annular ring 3350 are configured to avoid relying on a blade cutting edge 3342 as a stopping surface. Pushing or colliding a sharp cutting edge 3342 onto a guide surface 3225 for example may stop the advancement, but may also dull, damage or bend the blade 3340 inhibiting or frustrating accurate cutting into the native tendon 50. It may also cause nicks in the reusable guide 3200 over repeated uses. FIG. 6B shows a top view with the leading cutting edge 3342 of blade 3340 slightly spaced away axially in a distal direction relative to edge 3225 of guide 3200, when the annular ring 3350 is engaged with goal post 3240. FIG. 6C illustrates the corresponding location of the goal post 3240 and annular ring 3350 relative to each other when the blades are in the location shown in FIG. 6B. This proximal most extent defines a proximal most extent of cut along the native tendon 50 and the maximum length of the tendon graft. This may be predetermined based on the available length of native tendon 50 or target length required for the subsequent repair with this prepared tendon graft.

FIGS. 6A-6C illustrates the guide 3200 and harvesting tool 3300 interacting with the retractor 1100 removed from the figures for ease of understanding. In use, the guide 3200 may be operatively coupled to the retractor 1100, as shown in FIG. 6D. A portion of the retractor 1100 is removed from the illustration in FIG. 6D for convenience of understanding. FIG. 6D illustrates the harvesting tool 3300 in the proximal most location, with blades 3340 projecting through at least one of the openings through retractor 1100 and into the native tendon 50 50. Reference marking 3235*a* is disposed adjacent a distal edge 1121 of retractor 1100 and goal post 3240 is proximal to and external to the retractor 1100.

Figure 5A:
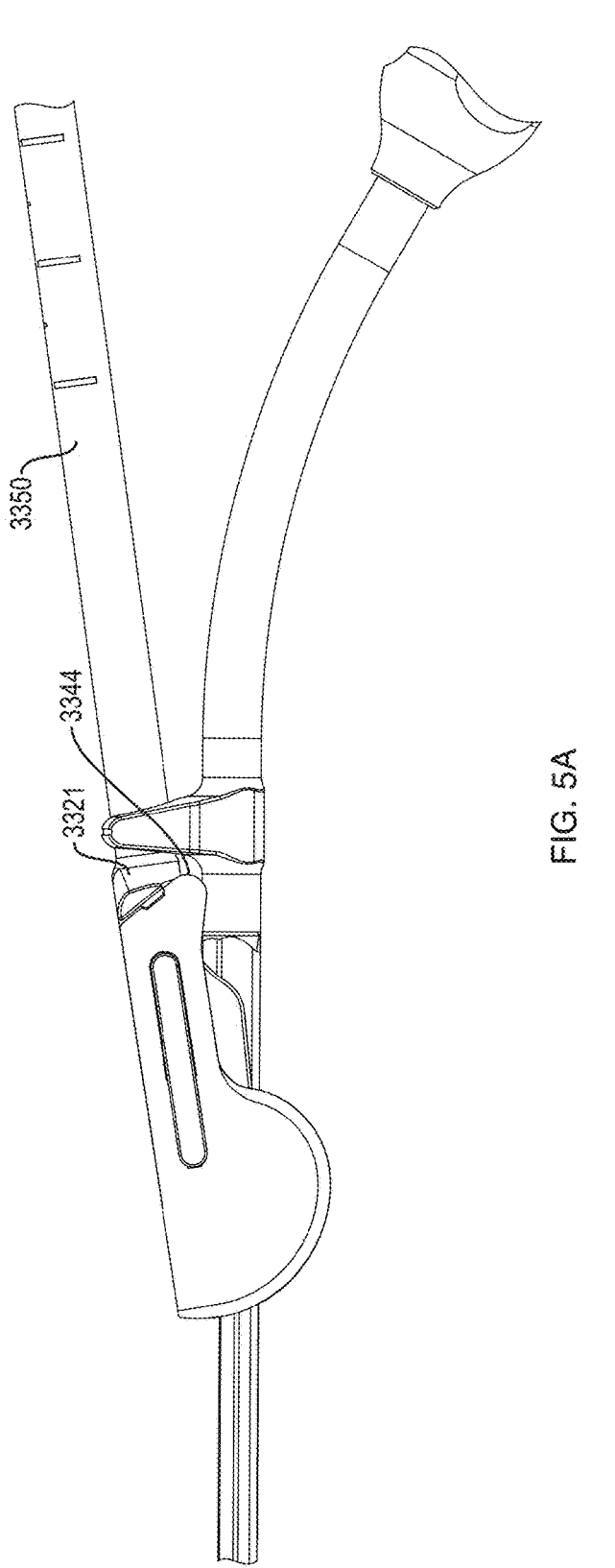
FIG. 5A illustrates a side view of the guide with the harvesting tool at a distal limit its translation, and a distal surface of the harvesting tool housing engaged with the goal post, in accordance with this disclosure.
Figure 5B:
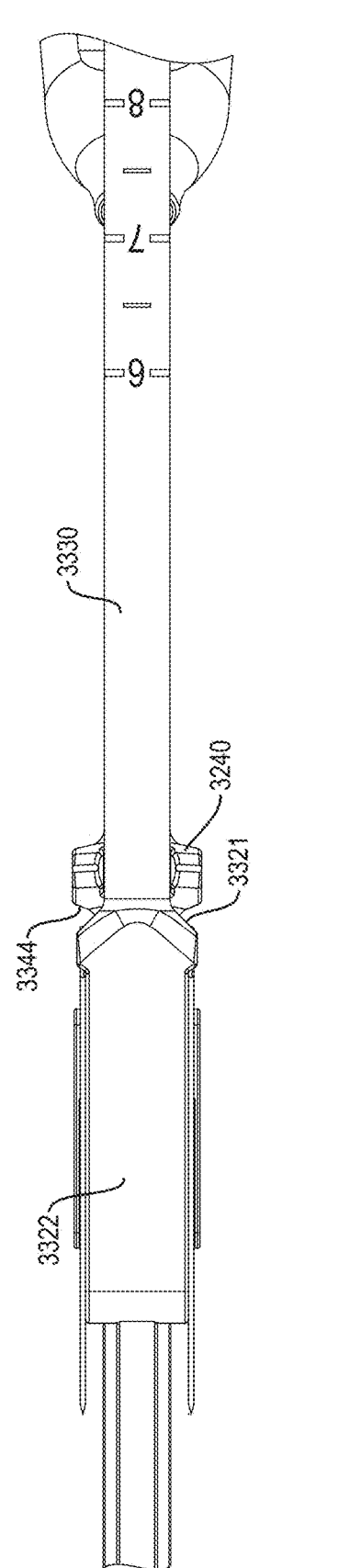
FIG. 5B illustrates a top-down view of the guide with the harvesting tool at the distal limit of its translation and with a distal surface of the harvesting tool housing engaged with the goal post, in accordance with this disclosure.
Figure 5C:
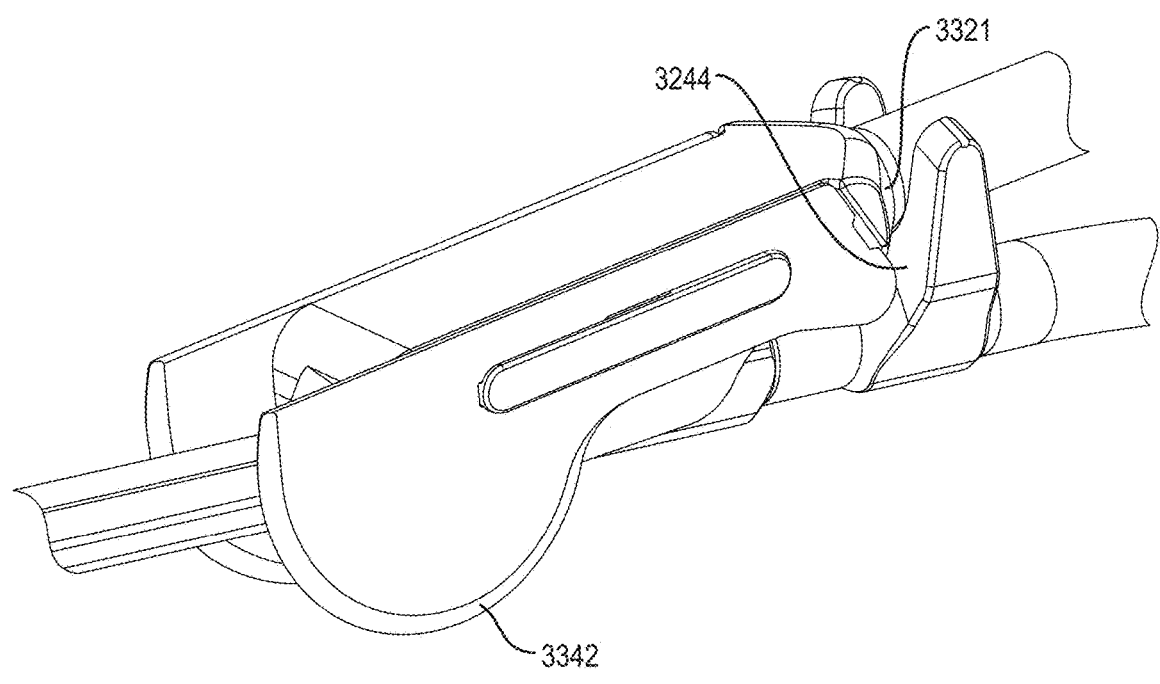
FIG. 5C illustrates a close-up perspective view of the guide goal post with the harvesting tool at the distal limit of its translation, with a distal surface of the harvesting tool housing engaged with the goal post, in accordance with this disclosure.
Figure 5D:
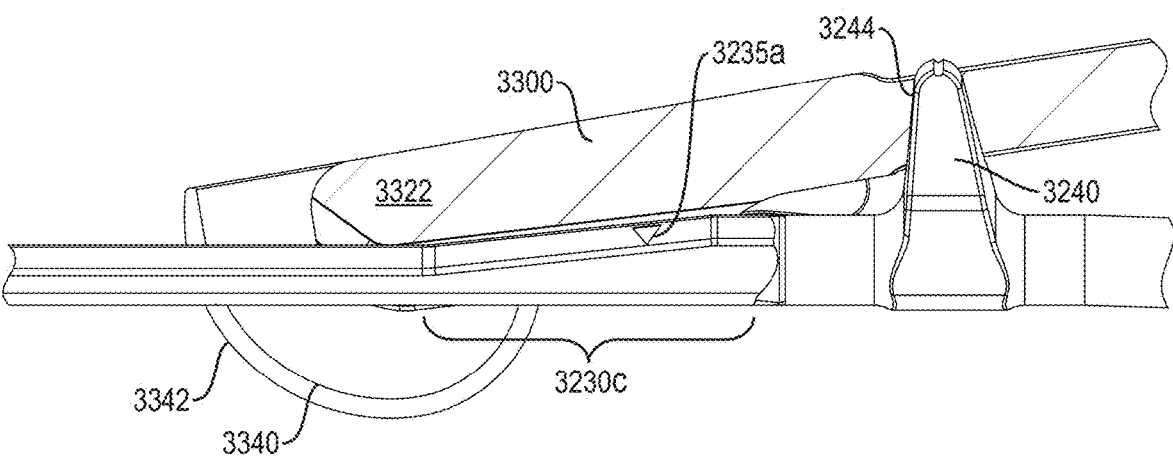
FIG. 5D illustrates a longitudinal cross section of FIG. 5C, in accordance with this disclosure.
Figure 5E:
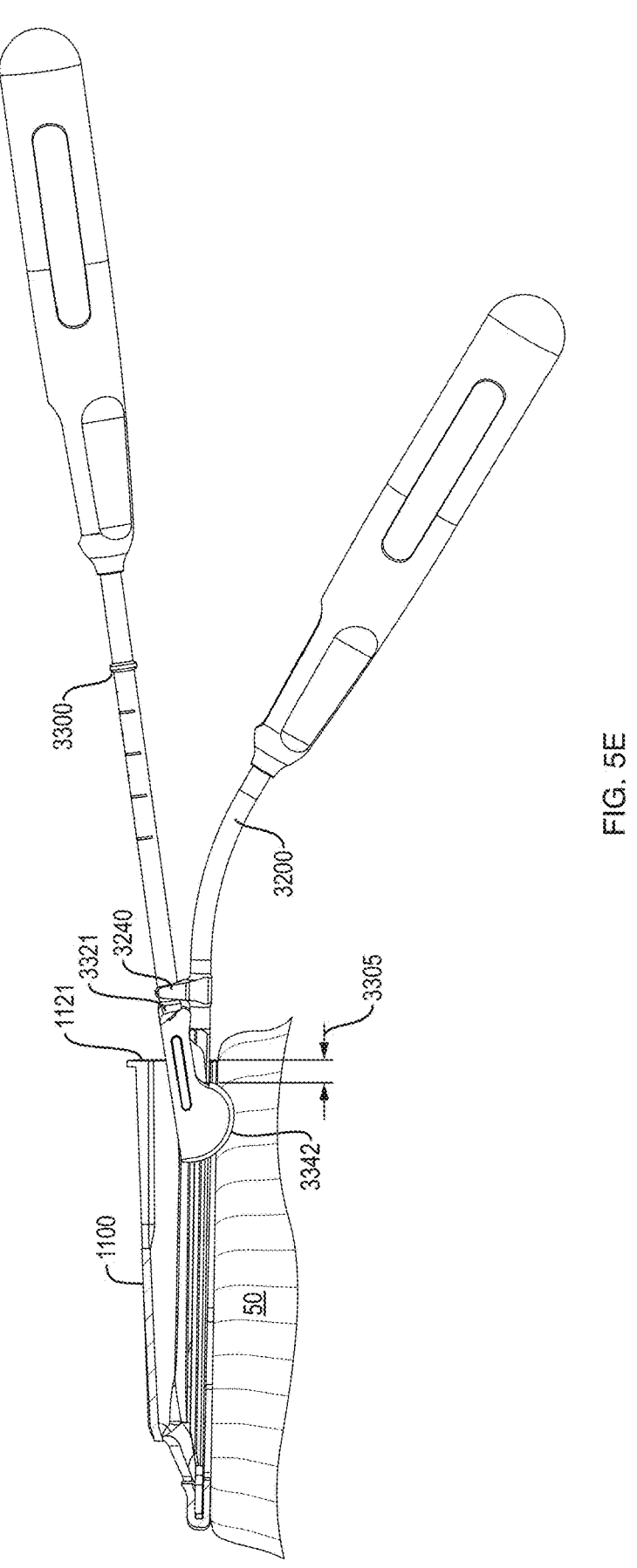
FIG. 5E illustrates a side view of the system with a portion of the retractor removed for observation of the harvesting tool at the distal limit of its translation relative to the retractor, in accordance with this disclosure.

A distal limit (nearest the knee) to the translational extent may also at least partially be defined by the goal post 3240. This is shown throughout the various views in FIGS. 5A-5E, where a distal facing surface 3321 of housing 3322 is configured to engage surface 3244 of goal post 3240 and prevent further retraction of harvesting tool 3300. Distal facing surface 3321 may define bilateral surfaces, extending laterally from shaft 3330 on both sides. Distal facing surfaces 3321 may face the handle 3310 and may extend at an incline relative to a harvesting tool shaft longitudinal axis. FIG. 5B illustrates a top view of housing 3322 with the distal facing surface 3321 engaging goal post 3240. FIG. 5C illustrates a close up view of housing 3320 with a distal facing surface 3321 engaging goal post 3240. FIG. 5D illustrates a cross section view of the harvesting tool 3300 relative to the guide tapered shaft portion 3230*c*. As explained earlier, as the housing 3322 approaches the distal end of guide shaft 3230, it is preferable that the cutting depth into the native tendon 50 become shallower. Tapered portion 3230*c* defines this taper in cutting depth. In reverse, as the blade 3340 is advanced towards the proximal end, this taper also forms a lead in for the cutting edge 3342 to enter the distal end of native tendon 50. Distal limit is also configured to stop the cutting edge 3340 from cutting too far distally, and damaging tissue at the knee end of native tendon 50. The native tendon 50 may become thinner as it extends distally, and therefore there may be less depth of native tendon 50 available. This tapered portion 3230*c* accommodates for this native tendon anatomy. Seen best in FIG. 5E, a distal most edge of cutting edge 3342 that engages the native tendon 50 is stopped from further distal translation by engagement between goal post 3240 and distal surface 3321 at a location that is proximally spaced 3305 from proximal edge 1121 of retractor 1100. In order to further retract the harvesting tool 3300, the harvesting tool 3300 is now preferably required to be lifted and removed from the native tendon 50. FIGS. 5A-5D illustrates guide 3200 and harvesting tool 3300 with the retractor 1100 removed from the figures for ease of understanding. Any of these figures may include the retractor, 1100, as illustrated in FIG. 5E. In FIG. 5E, the guide 3200 and harvesting tool 3300 are illustrated within the retractor 1100, with the guide 3200 operatively coupled to a proximal end of the retractor 1100 as disclose herein. A portion (front half) of the retractor 1100 is removed from the illustration for convenience of understanding.

Turning now to FIGS. 7, 8A-8D and FIG. 9, the system 3000 may also include a second harvesting tool, hereinafter called a proximal cutter 3400. Proximal cutter 3400 is configured to form an optional posterior cut along the native tendon 50 and also transect a proximal end of the tendon graft strip. Proximal cutter 3400 may be used with the guide 3200 and harvesting tool 3300 removed from the space defined by the retractor 1100. Proximal cutter 3400 may be similar to a proximal cutter disclosed in Patent Application PCT/US2021/036566, filed Jun. 9, 2021, and titled "SYSTEM AND METHOD FOR HARVESTING A TENDON"; commonly owned and herein incorporated by reference in its entirety, except where noted herein. The transecting operation occurs furthest from the skin incision making reliable cuts in the target area more difficult to achieve. Without the proximal cutter 3400, this cut end may be an uneven, jagged end, frustrating later suturing and coupling techniques. Proximal cutter 3400 forms a clean and uniform cut end, which makes later handling of the tendon graft easier. Proximal cutter 3400 includes a replaceable blade 3410 that is selectively operatively coupled to a working end 3450 of proximal cutter shaft 3440. Having a fresh blade 3410 for each procedure ensures consistent sharp edges and a more consistent and precise uniform slice through the fibrous tendon tissue. Sterilization methods of reusable instrument may tend to dull sharp edges.

Proximal cutter 3400 includes a handle end 3430 and a guillotine style cutter at working end 3450 of the cutter 3400. Shaft 3440 extends between the working end 3450 and handle end 3430. Shaft 3440 may include length estimation markers therealong and may include a static outer shaft and axially moveable inner pull rod 3436, which may be coaxially disposed along outer shaft. Working end 3450 may include a blade housing 3452. Inner pull rod 3436 is removably coupled to a blade 3410 and is configured to axially slide and selectively retract blade 3410, which transects any tissue disposed within an aperture of the blade 3410.

Figures 8A, 8B, 8C:
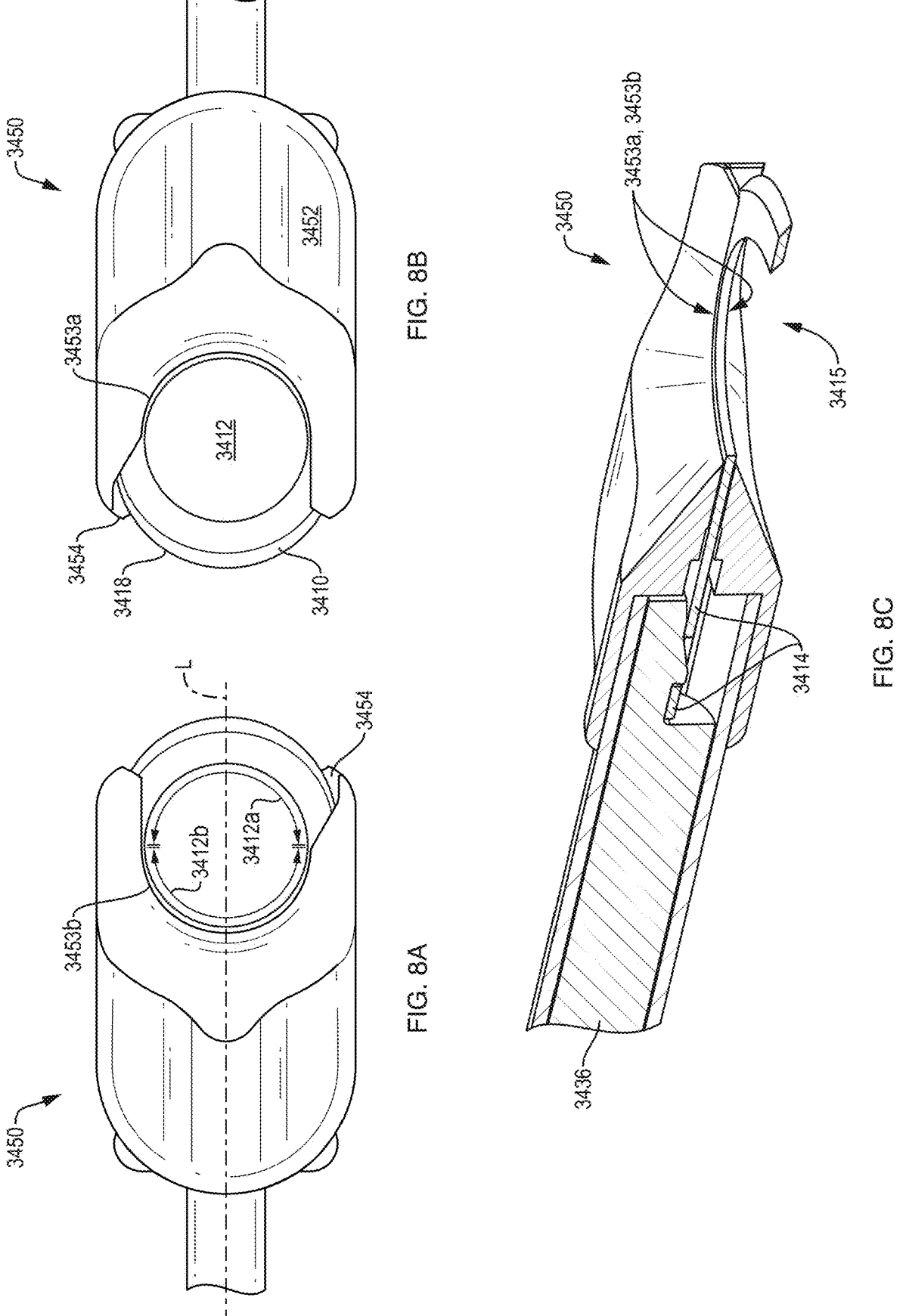
FIGS. 8A and 8B illustrate close up front and back views of a working end of the proximal cutter, in accordance with the disclosure.
FIG. 8C illustrates a cross section of the working end of the proximal cutter, in accordance with the disclosure.

FIGS. 8A and 8B show close up views of the front and back of working end 3450 with blade 3410 assembled within the working end housing. Blade 3410 is operatively coupled to rod 3436 (FIG. 8C). Blade 3410 defines a generally thin planar element with a connecting end 3414 (FIG. 8C) and cutting end 3415 extending therefrom. Cutting end 3415 includes an aperture 3412 configured to receive an end of a partially prepared tendon strip therethrough. The tendon strip may be partially prepared using harvesting tool 3300 to form at least two sides (lateral and medial sides) of the tendon strip. Aperture 3412 may define a 360 degree (°) bounded opening, with curved edges. Aperture 3412 may be oblong and sized to receive a tendon strip that includes a bone block therethrough. In this case, aperture 3412 may therefore define an opening size larger than the target graft strip width or cross section, as the bone block may be slightly larger and more rigid than the graft strip. This is termed a full thickness graft. Aperture 3412 may have an effective opening size that may be a diameter, configured to receive a graft and bone block up to 12 mm. Aperture 3412 may have an opening size that corelates with the harvesting tool housing width 3300 that defines the spacing between the two parallel blades (3340)

Aperture 3412 may have a boundary that includes at least one segment that is configured to cut the tendon tissue. Aperture boundary may include another segment that is configured to dissect loosely connected tissue but sufficiently blunt that is inhibited from cutting the tendon. More specifically aperture boundary may define an arc length

3412*a* that is sharp and therefore defines a cutting arc length 3412*a*. Arc length 3412*a* may transition to a blunter arc length 3412*b*. Arc lengths 3412*a* and 3412*b* may generally face each other, with the sharp arc length 3412*a* along a proximal side of aperture 3412, furthest from handle 3430. Aperture boundary may be disposed substantially along a plane that is parallel to and coincident with the device shaft longitudinal axis. Arc length 3412*b* may lie along a distal side of aperture 3412 and be disposed between and slightly proximally spaced from arced edges 3453*a*, 3452*b* of housing 3452. Arced edges 3453*a*, 3452*b* may be slightly recessed distally away from aperture edge 3412*b*. While arc length 3412*b* may be less sharp, arced edges 3453*a*, 3452*b* may define cutting edges that cooperate with proximal arc length 3412*a* during transection. Operation of these edges are discussed in more detail later.

Blade 3410 also includes a leading edge 3418 that defines a curved edge that is sufficiently sharp to define a cutting edge. Leading edge 3418 may form a posterior cut along the native tendon 50, while advancing proximally. Leading edge 3418 defines a convex curve. Leading edge 3418 may have a varying cutting profile along the curve. Leading edge 3418 may define a sharper cutting edge at the apex, coincident with the longitudinal axis of the device, that gradually reduces in effective sharpness as the edge 3418 extends laterally. Edge 3418 gradually tapers to a blunt edge at the location that blade edge 3418 enters the housing channel 3454. In operation, a distal end of a partially prepared tendon strip with the lateral and medial sides already formed is threaded through aperture 3412 with the leading edge 3418 disposed posteriorly relative to the QT anterior surface. The leading edge 3418 then may cut through the native tendon 50 and form a posterior side of the tendon graft strip as the cutter 3400 is advanced proximally. The depth of the posterior cut is limited by aperture 3412 size. While advancing the cutter 3400, distal arc length 3412*b* may bluntly disconnect smaller tissue bridges and loose connections between the anterior surface of the partially prepared tendon strip and adjacent tissues. The cutting edges 3453*a*, 3453*b* of housing 3452 are recessed away from distal arc length 3412*b* while advancing the cutter 3400 along the tendon, to protect tissue from these sharper edges (3453*a*, 3453*b*) while advancing the cutter 3400 proximally.

In summary therefore, cutter 3400 working end 3450 includes a plurality of edge surfaces to provide a plurality of separating and transecting functions while forming and harvesting the tendon tissue from the native tendon 50. In an open configuration, a partially formed tendon strip (lateral and medial sides formed) may be threaded through aperture 1412, and the working end 3450 advanced along the native tendon 50 to disconnect any loose connections between the anterior tendon surface via engagement of edge surface 3412*b*. While advancing working end 3450 along the native tendon 50, a posterior side of tendon strip or graft may also be concomitantly formed via engagement of edge surface 3418 with native tendon 50. When in the proximal most location along the native tendon 50, retraction of the blade 3410 may expose cutting surfaces 3453*a*, 3453*b* and also move the arc length edge 3412*a* of blade aperture 3412 towards cutting surfaces 3453*a*, 3453*b*. Arc length 3412*a* may move to be covered by housing 3422 and recessed within a slot disposed between the two cutting surfaces 3453*a*, 3453*b*, to transect the tendon, hereafter called the transected configuration.

Actuation of the handle 3430 retracts blade 3410 to cut the tendon tissue, and handle and actuation are similar to handle and mechanism disclosed in Patent Application PCT/

Figure 8D:
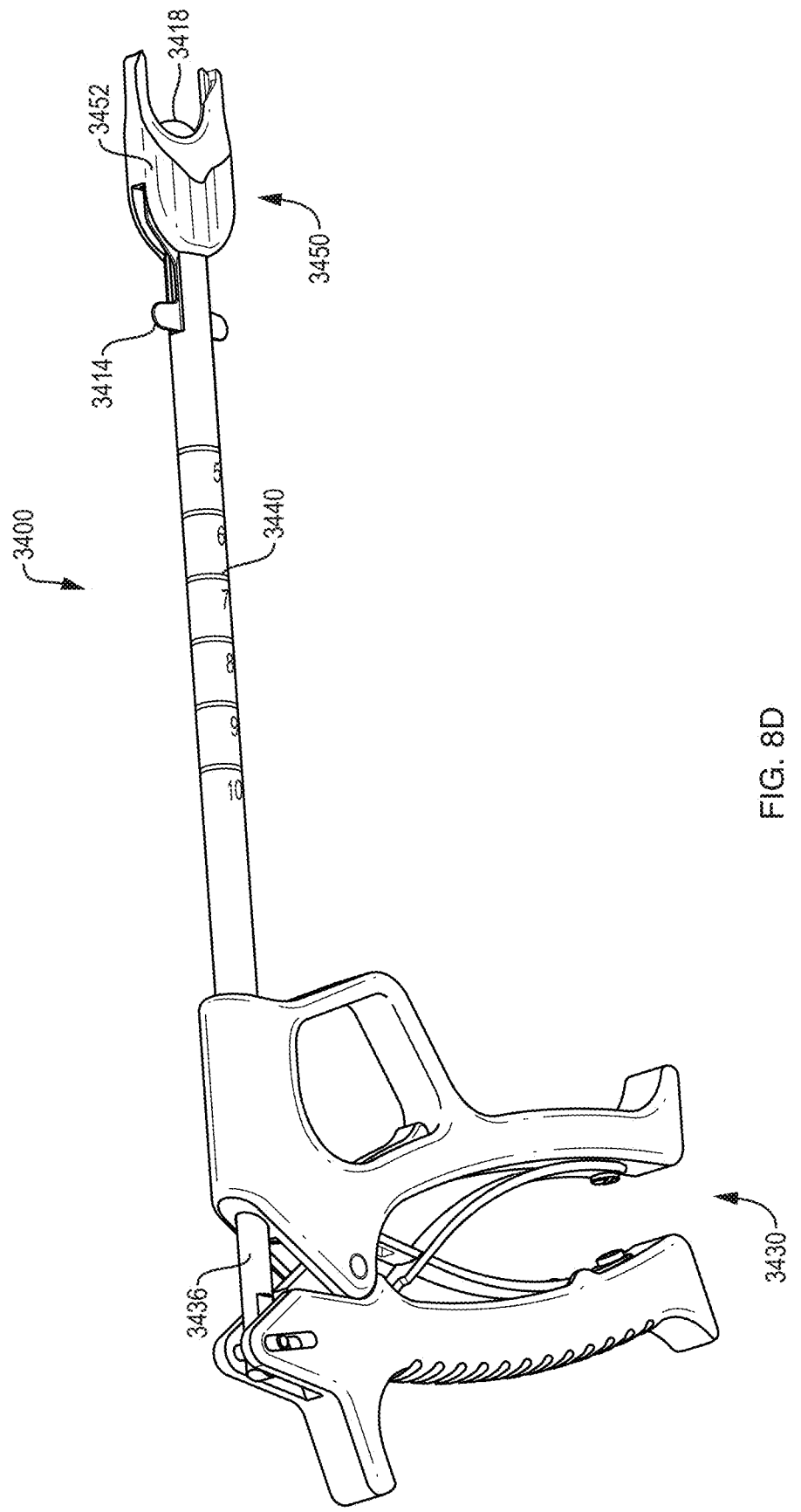
FIG. 8D illustrates the working end of the proximal cutter in a retracted configurated, in accordance with the disclosure.

US2021/036566, filed Jun. 9, 2021, and titled "SYSTEM AND METHOD FOR HARVESTING A TENDON"; commonly owned and herein incorporated by reference in its entirety. FIG. 8D illustrates the working end 3450 with the blade 3410 in a fully retracted configuration.

A method of forming a portion of the tendon graft is disclosed in figures throughout this disclosure, as well as FIGS. 9A-9D. The method may begin with making a minimally invasive incision at the superior pole of the patella, the incision shown in FIG. 9A. This incision 62 may be between 0.5-1 inches in length. Guide 3200 may then be inserted through incision 62 to dissect around the native tendon 50 to free the anterior surface of the native QT tendon (not shown). Guide 3200 may then be removed and coupled to retractor 1100. With the retractor 1100 and guide 3200 coupled, they may be inserted through skin incision 62 and along tendon 50, similar to the method disclosed in Patent Application PCT/US2021/036566, filed Jun. 9, 2021, and titled "SYSTEM AND METHOD FOR HARVESTING A TENDON"; commonly owned and herein incorporated by reference in its entirety.

This presents the surgeon with a retracted opening at the skin incision, corresponding with retractor distal opening 1120 with a tented working cavity and access to the tendon 50. Inserting may include deforming the retractor 1100 to fit though incision 62. Upon insertion, reference marking 3235a is disposed adjacent skin incision 62 seen best in FIG. 6D, and a length and width of available native tendon 50 may be estimated using markings 3235b. Based on these determinations, a working end configuration of a harvester 3300 may then be selected, including selecting a housing width (3322) and/or blade size. For example, a harvesting tool 3300 may be chosen, configured to form medial and lateral cuts along the native tendon 50, defining a tendon strip width of about 8 mm. Other widths may include a 10 mm wide strip, or a 12 mm wide strip. Harvesting tool 3300 may then be inserted through retractor end 1120 and into retractor working cavity. Harvesting tool shaft 3350 may be placed within projection channel 3246 of guide goal post, as shown in FIG. 5E. Harvesting tool housing 3322 also engages shaft 3230 of guide 3200 to guide trajectory of blades 3340 into and along the native tendon 50.

Figure 4B:
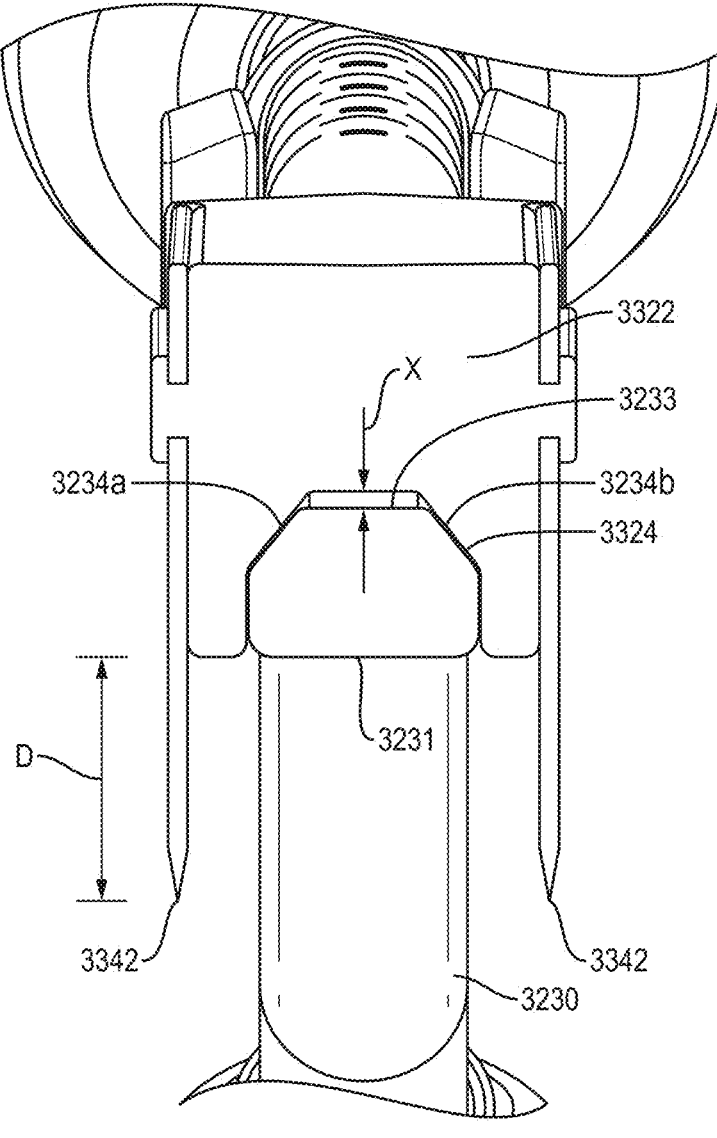
FIG. 4B illustrates a cross section of the guide shaft and harvesting tool housing, in accordance with this disclosure.

Housing 3320 covers a top surface 3233 of shaft 3230 while remaining spaced away, so as to reduce wear on the markings 3235b (FIG. 4B). The harvesting tool 3300 may then be advanced proximally to form medial and lateral sides of the graft strip from corresponding medial and lateral sides of the native tendon 50, simultaneously. Harvesting tool 3300 may include a channeled surface 3324 disposed between the two blades 3340 that slides along the guide shaft 3230 to limit the depth of cut into the native tendon 50 and also the trajectory of the two cuts along the native tendon 50 to the proximal end thereof. Harvesting tool 3300 may initially advance proximally along a tapered portion 3230c of the guide shaft 3230, to gradually increase the depth of cut into the native tendon 50. Harvesting tool 3300 may advance until an annular ring 3350 abuts goal post 3240 (FIG. 6D), wherein further proximal advancement is inhibited. Annular ring 3350 may abut goal post 3240 (FIG. 6D), at a translational extent that protects the blade edges from being damaged by the guide 3200. The harvesting tool 3300 may define a continuous curved blade edge such that retraction of the harvesting tool 3300 along the static guide shaft 3230, towards the knee may also form lateral sides of the tendon strip, or at least separate some remaining tissue bridges between the strip sides and remaining native tendon 50. The guide shaft 3230 may be tapered so that during retraction of the harvesting tool 3300 along this tapered portion 3230C a depth of cut into the tendon gradually becomes shallower. This tapered portion 3230c may extend through a distal opening of retractor 1100, when the retractor and dissector 3200 are operatively coupled. Harvesting tool 3300 may be retracted towards the knee until a surface 3321 of the harvesting tool 3300 abuts the goal post 3240, limiting the distal translational extent of the blade 3340. At this limit, the blade edge 3342 is entirely spaced proximally from distal opening of retractor 1100, to protect the tissues around the knee. The harvesting tool channel 3324 may be contoured such that a depth of cut into the tendon 50 is relatively consistent along the length of the cuts, despite the angle of approach of the harvesting tool 3300.

Figure 9B:
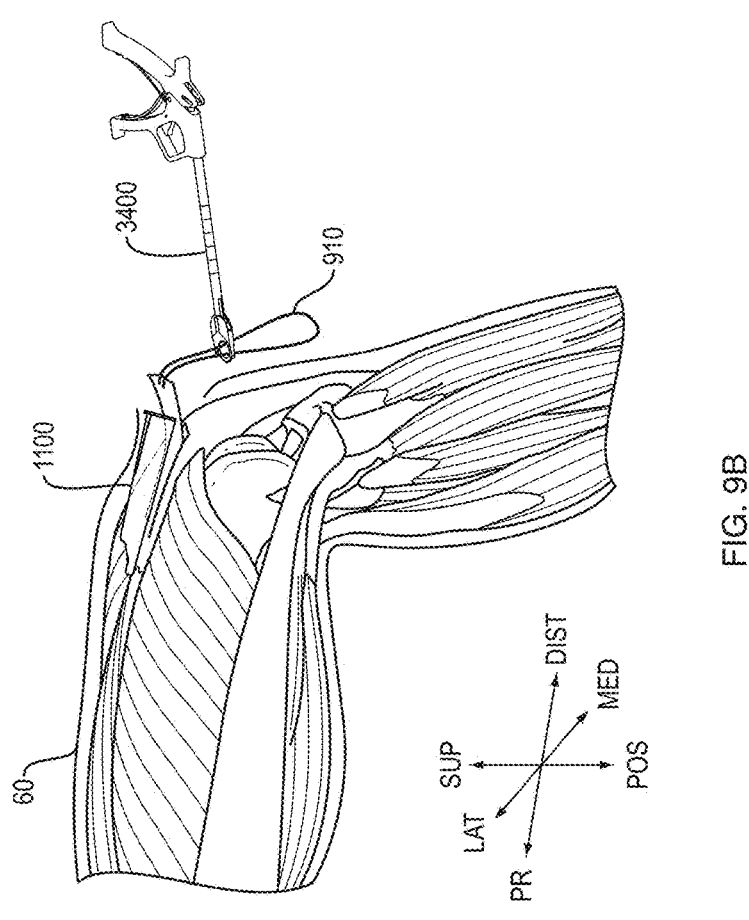
FIGS. 9A-9F illustrate forming a portion of a tendon strip from a native tendon using the proximal cutter.
Figure 9A:
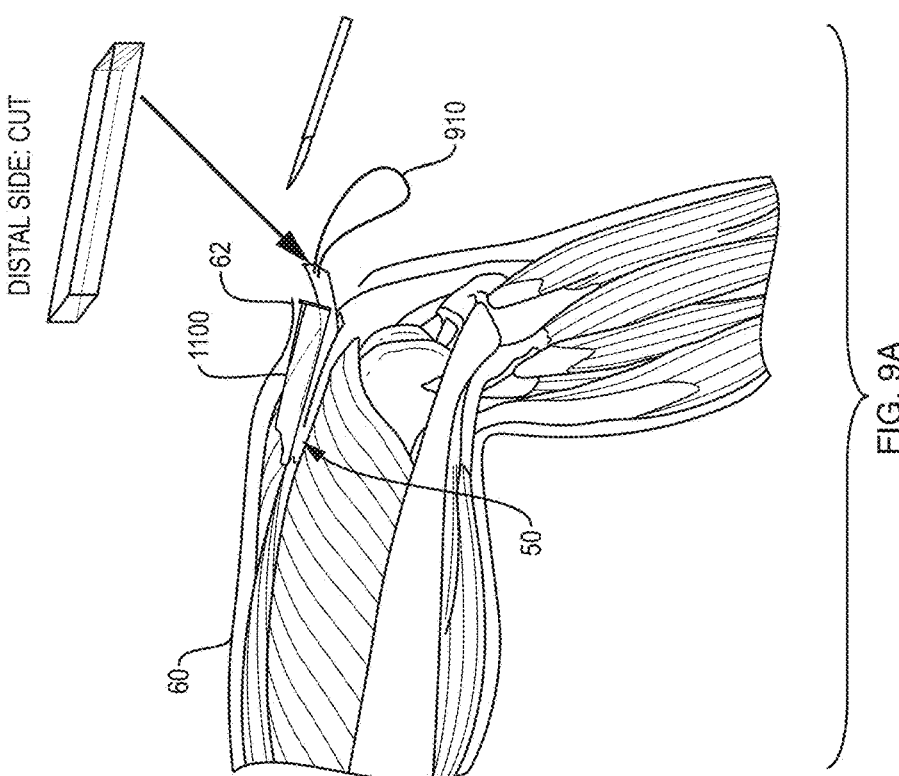
Figures 9C, 9D, 9E:
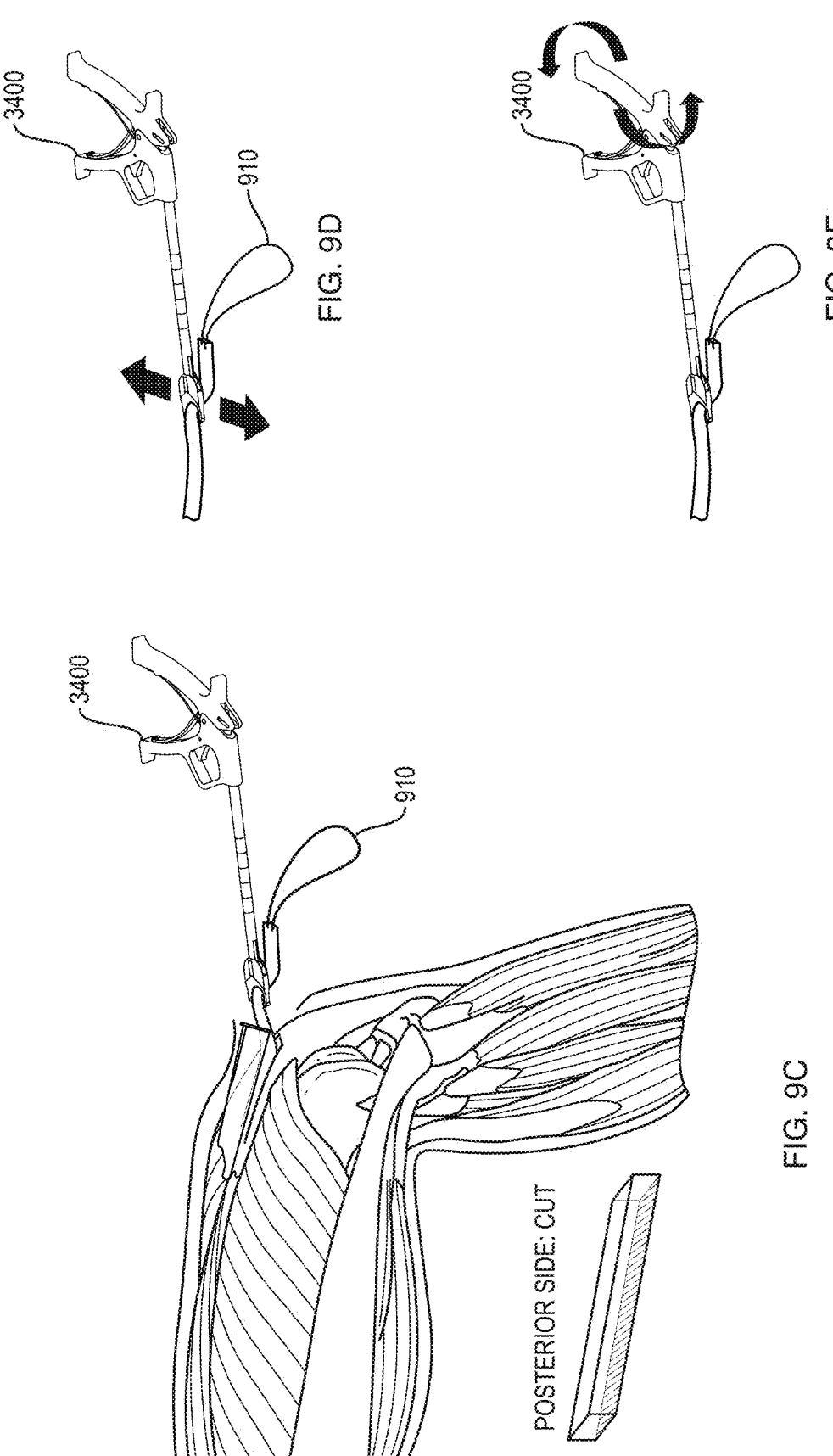
Figure 9F:
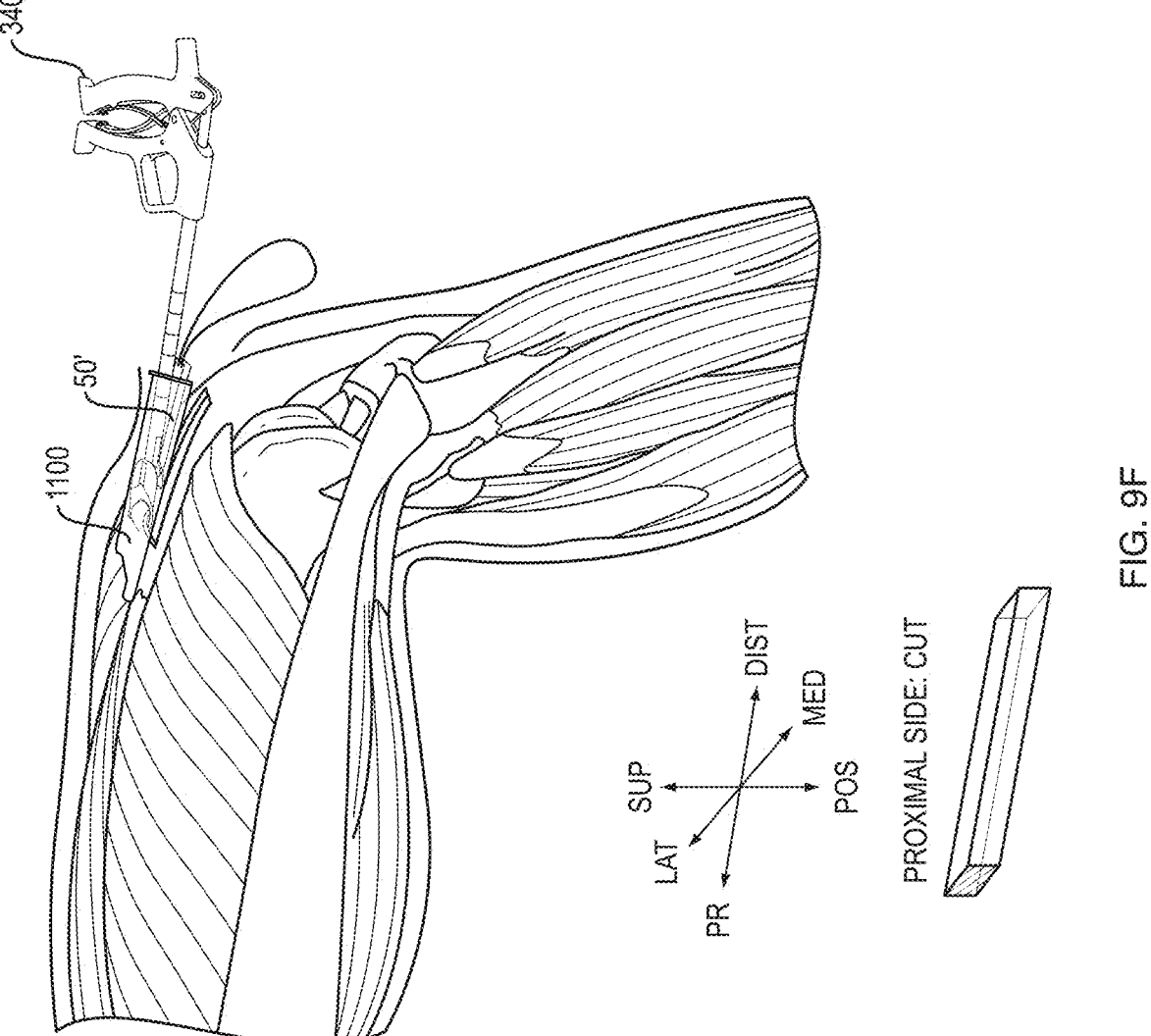

The guide 3200 and harvesting tool 3300 may then be removed, leaving the retractor 1100 in situ. The medial and lateral side surfaces of the tendon strip are now separated from the native tendon 50. The proximal and posterior separation may then be performed with the proximal cutter 3400, represented in FIGS. 9A-9F. FIG. 9A illustrates a patient knee with the retractor 1100 in situ and the two lateral sides of the graft already formed. Some distal separation may be performed with a scalpel, with the retractor 1100 remaining in place. A suture 910 may be stitched through a distal end of tendon graft to maintain tension on the tendon graft. This suture 910 may be formed in a loop and ends of the suture 920 may then be threaded through aperture 3412 of proximal cutter (FIG. 9B) so as to place the leading edge 3418 posterior to the QT anterior surface. Cutter 3400 may be pushed proximally with tension on the tendon (via looped suture) to form a posterior cut along the QT on the posterior side of the graft and disconnect any remaining loose tissue bridges from the tendon anterior surface (FIG. 9C). While advancing, the cutter 3400 may be rocked back and forth in a "windshield wiper" fashion (FIG. 9D) or "walking the dog" fashion to help in advancing through the tendon (FIG. 9E). While advancing, the resulting tendon strip 50' may be fed through aperture 3412. The resultant strip 50' may loop over cutting edge 3418 and then into aperture 3412 and under proximal cutter shaft 3440. Working end 3450 may extend through retractor end 1120 along tendon strip 50' to the proximal end of native tendon 50, illustrated in FIG. 9F. A lock out member of proximal cutter 3400 may then be moved and the proximal cutter 3400 actuated to amputate the graft strip. Blade 3410 is retracted into housing 3452 to amputate the tendon strip. Tendon strip, proximal cutter 3400 and retractor 3100 may then be removed.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

We claim:

1. A surgical device for harvesting a tendon graft strip from a native tendon comprising:
   a handle;
   a shaft extending from the handle, the shaft having a central longitudinal axis; and
   a housing extending from the shaft;
   a blade operatively coupled to the shaft, the blade defining a thin planar element and including:

an aperture extending though through a thickness of the blade, the aperture configured to receive the tendon graft strip therethrough, a boundary of the aperture including a cutting edge-surface, the aperture symmetrical about the central longitudinal axis; and a leading cutting edge-surface extending along a distal-most end of the blade, distally spaced from the aperture, the leading cutting edge-surface of the blade configured to form a posterior side of the tendon graft strip as the surgical device is advanced along the tendon graft strip;

wherein the blade is configured to axially slide relative to the housing between an open configuration and a transected configuration and wherein the leading cutting edge-surface of the blade is configured to form the posterior side of the tendon graft strip while the blade is in the open configuration, the leading cutting edge surface having a sharper cutting edge surface along a central portion of the leading cutting edge surface coincident with the central longitudinal axis and reduced sharpness extending laterally from the central portion.

2. The surgical device of claim 1 wherein in the open configuration, the blade is distally disposed relative to when in the transected configuration.

3. The surgical device of claim 1 wherein a distal edge of the housing defines a cutting-edge surface.

4. The surgical device of claim 1 wherein a distal edge of the housing defines a cutting-edge surface and wherein in the open configuration, the aperture is spaced distally from the housing cutting-edge surface, to shield the housing cutting-edge surface from the tendon graft strip.

5. The surgical device of claim 4 wherein when the blade is moved to the transected configuration, the housing cutting-edge surface becomes exposed to the tendon graft strip disposed within the aperture.

6. The surgical device of claim 4 wherein when the blade is moved to the transected configuration the aperture cutting-edge portion is configured to cooperate with the housing cutting-edge surface to transect the tendon graft strip.

7. The surgical device of claim 1 wherein axially sliding to the transected configuration includes axially retracting the blade towards the handle.

8. The surgical device of claim 1 wherein the blade leading cutting edge-surface defines the distal-most edge of the surgical device when the blade is in the open configuration.

9. The surgical device of claim 1 wherein the blade leading cutting edge-surface extends along a single plane that intersects a shaft longitudinal axis.

10. The surgical device of claim 9 wherein the leading cutting edge-surface is a convex curved edge surface that extends along the single plane.

11. A surgical device for harvesting a tendon graft strip from a native tendon comprising:
   a handle;
   a shaft extending from the handle; and
   a housing extending from the shaft, a distal edge of the housing having a cutting-edge surface;
   a blade operatively coupled to the shaft, the blade defining a thin planar element and including;

an aperture extending through the blade, the aperture having an opening configured to receive the tendon graft strip therethrough, the aperture defining a boundary that has a cutting edge-surface; and a leading cutting edge-surface at a distal-most end of the blade, distally spaced from the aperture, the leading cutting edge-surface of the blade configured to form a posterior side of the tendon graft strip as the surgical device is advanced along the tendon graft strip, the leading cutting edge surface having a sharper cutting edge surface along a central portion of the leading cutting edge surface coincident with a central longitudinal axis of the shaft and reduced sharpness extending laterally from the central portion.

12. The surgical device of claim 11 wherein the blade is configured to axially slide relative to the housing between an open configuration and a transected configuration.

13. The surgical device of claim 12 wherein the blade is configured to form a posterior side of the tendon graft when the blade is in the open configuration.

14. The surgical device of claim 12 wherein in the open configuration, the aperture is spaced distally of the housing cutting-edge surface, to shield the housing cutting-edge surface from the tendon graft strip.

15. The surgical device of claim 12 wherein when the blade is moved to the transected configuration, the housing cutting-edge surface becomes exposed to the tendon strip that is disposed within the aperture.

16. The surgical device of claim 12 wherein when the blade is moved to the transected configuration, the housing cutting-edge surface is configured to cooperate with the aperture cutting-edge surface to transect the tendon graft strip.

17. The surgical device of claim 11 wherein the leading cutting edge-surface is a convex curved edge surface that extends along a single plane, the convex curved edge surface having an apex coincident with the central longitudinal axis.

18. A surgical device for harvesting a tendon graft strip from a native tendon comprising:
   a handle;
   a shaft extending from the handle; and
   a housing extending from the shaft, a distal edge of the housing having a cutting-edge surface;
   a blade operatively coupled to the shaft, the blade defining a thin planar element and including;
   an aperture extending through the blade, the aperture having an opening configured to receive the tendon graft strip therethrough, the aperture defining a 360-degree bounded hole, wherein at least an edge segment of the bounded hole defines a cutting edge-surface; and
   a leading cutting edge-surface at a distal-most end of the blade, distally spaced from the aperture, the leading cutting edge-surface of the blade configured to form a posterior side of the tendon graft strip as the surgical device is advanced along the tendon graft strip;
   wherein the blade is configured to axially retract relative to the housing from an open configuration and a transected configuration, and wherein retracting the blade is configured to expose the housing cutting-edge surface to the tendon strip and transect the tendon graft strip.

* * * * *